(12) United States Patent
Shahinian

(10) Patent No.: US 9,861,261 B2
(45) Date of Patent: Jan. 9, 2018

(54) ENDOSCOPE SYSTEM AND METHOD OF OPERATION THEREOF

(71) Applicant: Hrayr Karnig Shahinian, Beverly Hills, CA (US)

(72) Inventor: Hrayr Karnig Shahinian, Beverly Hills, CA (US)

( * ) Notice: Subject to any disclaimer, the term of this patent is extended or adjusted under 35 U.S.C. 154(b) by 359 days.

(21) Appl. No.: 14/658,187

(22) Filed: Mar. 14, 2015

(65) Prior Publication Data

US 2015/0257629 A1 Sep. 17, 2015

Related U.S. Application Data

(60) Provisional application No. 61/953,718, filed on Mar. 14, 2014.

(51) Int. Cl.
*A61B 1/00* (2006.01)
*A61B 1/05* (2006.01)
(Continued)

(52) U.S. Cl.
CPC ...... *A61B 1/00087* (2013.01); *A61B 1/00133* (2013.01); *A61B 1/05* (2013.01);
(Continued)

(58) Field of Classification Search
CPC ... A61B 1/00087; A61B 1/05; A61B 1/00133; A61B 1/00183; A61B 90/361;
(Continued)

(56) References Cited

U.S. PATENT DOCUMENTS

| 1,960,011 A | 5/1934 | Ives |
| 2,255,631 A | 9/1941 | Shulman |

(Continued)

FOREIGN PATENT DOCUMENTS

| EP | 0469966 B1 | 2/1992 |
| EP | 1371321 A1 | 12/2003 |

(Continued)

OTHER PUBLICATIONS

Y.S. Heo, "Illumination and Camera Invariant Stereo Matching," Computer Vision and Pattern Recognition, 2008. CVPR 2008. IEEE Conference, vol. No. pp. 1-8, Jun. 23-28, 2008.

(Continued)

*Primary Examiner* — Timothy J Neal

(57) ABSTRACT

An endoscopic microinstrument may include a substantially rigid body having first and second ends, a channel between the first and second ends; a substantially rigid end portion movably coupled to the body and having first and second ends; a tool located at the first end of the end portion and including first and second anvils; first and second handles coupled to the body, at least one of the handles further coupled to the tool and configured to control actuation of at least one of the first and second anvils; a camera coupled to, and situated to a side of, the substantially rigid end portion, the camera configured to obtain images of a region-of-interest; and an end portion controller coupled to the body and configured angulate and/or rotate the substantially rigid end portion relative to the substantially rigid body.

16 Claims, 16 Drawing Sheets

(51) Int. Cl.
*A61B 17/29* (2006.01)
*A61B 90/00* (2016.01)
A61B 1/04 (2006.01)
A61B 17/00 (2006.01)
A61B 17/22 (2006.01)

(52) U.S. Cl.
CPC .......... *A61B 17/29* (2013.01); *A61B 90/361* (2016.02); *A61B 1/00183* (2013.01); *A61B 17/22012* (2013.01); *A61B 2017/003* (2013.01); *A61B 2017/00221* (2013.01)

(58) Field of Classification Search
CPC .............. A61B 17/29; A61B 17/22012; A61B 2017/00221; A61B 2017/003
See application file for complete search history.

(56) References Cited

U.S. PATENT DOCUMENTS

| | | | |
|---|---|---|---|
| 3,870,037 A | 3/1975 | Cadariu et al. |
| 4,651,201 A | 3/1987 | Schoolman |
| 4,759,348 A | 7/1988 | Cawood |
| 4,761,066 A | 8/1988 | Carter |
| 4,873,572 A | 10/1989 | Miyazaki et al. |
| 4,877,307 A | 10/1989 | Kalmanash |
| 4,951,676 A | 8/1990 | Collet-Billon |
| 5,050,226 A | 9/1991 | Collet-Billon |
| 5,105,269 A | 4/1992 | Nakamura et al. |
| 5,192,969 A | 3/1993 | Igarashi et al. |
| 5,222,477 A | 6/1993 | Lia |
| 5,305,098 A | 4/1994 | Matsunaka et al. |
| 5,395,030 A | 3/1995 | Kuramoto et al. |
| 5,436,655 A | 7/1995 | Hiyama et al. |
| 5,459,605 A | 10/1995 | Kempf |
| 5,471,237 A | 11/1995 | Shipp |
| 5,494,483 A | 2/1996 | Adair |
| 5,536,234 A | 7/1996 | Newman |
| 5,540,229 A | 7/1996 | Collet-Billon et al. |
| 5,547,455 A | 8/1996 | McKenna et al. |
| 5,603,687 A | 2/1997 | Hori et al. |
| 5,605,532 A | 2/1997 | Schermerhorn |
| 5,662,584 A | 9/1997 | Hori et al. |
| 5,667,473 A | 9/1997 | Finn et al. |
| 5,697,891 A | 12/1997 | Hori |
| 5,743,847 A | 4/1998 | Nakamura et al. |
| 5,751,341 A | 5/1998 | Chaleki et al. |
| 5,782,752 A | 7/1998 | Lichtman et al. |
| 5,810,716 A | 9/1998 | Mukherjee et al. |
| 5,817,014 A | 10/1998 | Hori et al. |
| 5,823,940 A | 10/1998 | Newman |
| 5,827,323 A | 10/1998 | Klieman et al. |
| 5,828,487 A | 10/1998 | Greening et al. |
| 5,835,194 A | 11/1998 | Morton |
| 5,841,887 A | 11/1998 | Kuwayama et al. |
| 5,855,549 A | 1/1999 | Newman |
| 5,895,350 A | 4/1999 | Hori |
| 5,928,137 A | 7/1999 | Green |
| 5,935,057 A | 8/1999 | Lichtman et al. |
| 5,941,817 A | 8/1999 | Crawford |
| 5,941,818 A | 8/1999 | Hori et al. |
| 5,944,654 A | 8/1999 | Crawford |
| D415,146 S | 10/1999 | Hori |
| 5,964,696 A | 10/1999 | Mihalca et al. |
| 5,984,939 A | 11/1999 | Yoon |
| 5,989,182 A | 11/1999 | Hori et al. |
| 6,046,727 A | 4/2000 | Rosenberg et al. |
| 6,050,939 A | 4/2000 | Pak Wai |
| 6,066,090 A | 5/2000 | Yoon |
| 6,086,528 A | 7/2000 | Adair |
| 6,159,146 A | 12/2000 | El Gazayerli |
| 6,191,809 B1 | 2/2001 | Hori et al. |
| 6,211,848 B1 | 4/2001 | Plesniak et al. |
| 6,223,100 B1 | 4/2001 | Green |
| 6,277,064 B1 | 8/2001 | Yoon |
| RE37,356 E | 9/2001 | Hori et al. |
| 6,290,649 B1 | 9/2001 | Miller et al. |
| 6,292,221 B1 | 9/2001 | Lichtman |
| 6,306,082 B1 | 10/2001 | Takahashi et al. |
| 6,313,883 B1 | 11/2001 | Thaler |
| 6,419,626 B1 | 7/2002 | Yoon |
| 6,445,814 B2 | 9/2002 | Iijima et al. |
| 6,450,948 B1 | 9/2002 | Matsuura et al. |
| 6,450,950 B2 | 9/2002 | Irion |
| 6,517,479 B1 | 2/2003 | Sekiya et al. |
| 6,593,957 B1 | 7/2003 | Christie |
| 6,624,935 B2 | 9/2003 | Weissman et al. |
| 6,647,792 B2 | 11/2003 | Ogawa |
| 6,731,988 B1 | 5/2004 | Green |
| 6,817,973 B2 | 11/2004 | Merril et al. |
| 6,832,984 B2 | 12/2004 | Stelzer et al. |
| 6,916,286 B2 | 7/2005 | Kazakevich |
| 6,976,956 B2 | 12/2005 | Takahashi et al. |
| 6,980,676 B2 | 12/2005 | Pineau |
| 6,991,602 B2 | 1/2006 | Nakazawa et al. |
| 6,997,871 B2 | 2/2006 | Sonnenschein et al. |
| 7,043,062 B2 | 5/2006 | Gerard et al. |
| RE39,342 E | 10/2006 | Starks et al. |
| 7,153,259 B2 | 12/2006 | Matsuzawa et al. |
| 7,154,527 B1 | 12/2006 | Goldstein et al. |
| 7,241,262 B2 | 7/2007 | Adler et al. |
| 7,553,277 B2 | 6/2009 | Hoefig et al. |
| 7,601,119 B2 | 10/2009 | Shahinian |
| 7,621,869 B2 | 11/2009 | Ratnakar |
| 7,803,137 B2 * | 9/2010 | Stefanchik .......... A61B 1/00073 604/174 |
| 2002/0030678 A1 | 3/2002 | Ostermann |
| 2002/0049367 A1 * | 4/2002 | Irion ................. A61B 1/00183 600/173 |
| 2002/0154215 A1 | 10/2002 | Schechterman et al. |
| 2003/0053744 A1 | 3/2003 | Makio |
| 2003/0125608 A1 | 7/2003 | Igarashi |
| 2003/0174208 A1 | 9/2003 | Glukhovsky et al. |
| 2003/0233024 A1 | 12/2003 | Ando |
| 2004/0019255 A1 | 1/2004 | Sakiyama |
| 2004/0070667 A1 | 4/2004 | Ando |
| 2004/0249367 A1 | 12/2004 | Saadat et al. |
| 2005/0065657 A1 | 3/2005 | Green |
| 2005/0065658 A1 | 3/2005 | Green |
| 2005/0119530 A1 | 6/2005 | Douglas et al. |
| 2005/0228230 A1 | 10/2005 | Schara et al. |
| 2005/0234296 A1 | 10/2005 | Saadat et al. |
| 2005/0234297 A1 | 10/2005 | Devierre et al. |
| 2005/0261548 A1 | 11/2005 | Machiya et al. |
| 2005/0278711 A1 | 12/2005 | Silva et al. |
| 2006/0015008 A1 | 1/2006 | Kennedy |
| 2006/0020287 A1 | 1/2006 | Lee et al. |
| 2006/0111614 A1 | 5/2006 | Saadat et al. |
| 2006/0224040 A1 | 10/2006 | Khait et al. |
| 2006/0247495 A1 | 11/2006 | Bacher et al. |
| 2007/0055103 A1 | 3/2007 | Hoefig et al. |
| 2007/0112256 A1 | 5/2007 | Terakawa et al. |
| 2007/0173689 A1 | 7/2007 | Ozaki et al. |
| 2007/0249932 A1 | 10/2007 | Shahinian |
| 2007/0255100 A1 | 11/2007 | Barlow et al. |
| 2008/0281154 A1 | 11/2008 | Gono et al. |
| 2008/0284982 A1 | 11/2008 | Richards et al. |
| 2009/0137893 A1 | 5/2009 | Seibel et al. |
| 2009/0187072 A1 | 7/2009 | Manohara et al. |
| 2010/0006549 A1 | 1/2010 | Pahk et al. |
| 2011/0115882 A1 | 5/2011 | Shahinian et al. |
| 2013/0023872 A1 * | 1/2013 | Mueller ............... A61B 17/29 606/34 |
| 2016/0220313 A1 * | 8/2016 | Durvasula .......... A61B 1/00098 |

FOREIGN PATENT DOCUMENTS

| | | |
|---|---|---|
| EP | 1854420 A1 | 11/2007 |
| EP | 1880657 A1 | 1/2008 |
| EP | 1989990 A1 | 11/2008 |
| JP | 04-021105 | 1/1992 |
| JP | 06-202004 | 7/1994 |
| JP | 06-237892 | 8/1994 |
| JP | 10-010468 | 1/1998 |

(56) References Cited

FOREIGN PATENT DOCUMENTS

| | | |
|---|---|---|
| JP | 2000-052289 | 2/2000 |
| WO | 93/13916 A1 | 7/1993 |
| WO | 96/35975 A1 | 11/1996 |
| WO | 99/57900 A1 | 11/1999 |
| WO | 00/50927 A2 | 8/2000 |
| WO | 00/61009 A1 | 10/2000 |
| WO | 0237142 A2 | 5/2002 |
| WO | 03098913 A2 | 11/2003 |
| WO | 2005/030328 A2 | 4/2005 |
| WO | 2005/031433 A1 | 4/2005 |
| WO | 2005/120327 A2 | 12/2005 |
| WO | 2008/033356 A2 | 3/2008 |

OTHER PUBLICATIONS

J.L. Garb, "Using GIS for spatial analysis of rectal lesions in the human body," International Journal of Health Geographies, 2007, 6:11, Published online Mar. 15, 2007. doi: 10.1186/1476-072X-6-11. PMCID: PMC1839078 BioMed Central Ltd.

J.P. Rice, "A hyperspectral image projector for hyperspectral imagers," SPIE vol. 6565 65650C, (2007).

J.P. Rice, "Hyperspectral image projectors for radiometric applications," BIPM and IOP Publishing Ltd, Metrologia 43 (2006) S61-S65.

J.P. Rice, "Development of hyperspectral image projectors," SPIE vol. 6297, 629701, (2006).

J.M. Medina, "Binocular interactions in random chromatic changes at isoluminance," Opt. Soc. Am., 2006, vol. 23, No. 2, pp. 239-246.

A. Szold, "Seeing is believing-Visualization systems in endoscopic surgery (video, HDTV, stereoscopy, and beyond)," Surgical Endoscopy, 19:55, pp. 730-733, Springer, 2005.

U. D. A Mueller-Richter, "Possibilities and limitations of current stereo-endoscopy," Journal of Surgical Endoscopy, Springer, New York, ISSN 0930-2794 (Print) 1432-2218 (Online) Issue vol. 18, No. 6, Jun., 2004, 18: pp. 942-947.

M.A. Weissman, "Stereo parallax and Disnparity in Single-Lens Stereoscopy," Stereoscopic Displays and Virtual Reality Systems VII, SPIE 3987, pp. 312-320, Apr. 2000.

G.A. Lester, "Ferroelectric liquid crystal device for a single camera stereoscopic endoscope system," Electronics Letters, 1997, vol. 33, No. 10, pp. 857-858.

G.L. Zimmerman, "Perception at Equiluminance: An Adaptive Model of Motion Metamers," Circuits and Systems, 1994., Proceedings of the 37th Midwest Symposium on , vol. 1, No. pp. 577-580 vol. 1, Aug. 3-5, 1994.

Y. Takemura, "Stereoscopic Video Movie Camera Using 300k Pixel IT-CCD Sensors," IEEE Transactions on Consumer Electronics, Feb. 1991, vol. 37, No. 1, pp. 39-44.

E. Badique, "Use of color image correlation in the retrieval of gastric surface topography by endoscopic stereopair matching," Applied Optics, 1988, vol. 27, No. 5, pp. 941-948.

N. Ohyama, "Compensation of motion blur in CCD color endoscope images," Opt. Soc. Am., 2006, Applied Optics, 1987, vol. 26, No. 5, pp. 909-912.

P. Breedveld and M. Wentink, "Eye-hand coordination in laparoscopy—an overview of experiments and supporting aids," Min Invas Ther & Allied Technol 2001: 155-162, 10(3).

Keijirou Itakura, et al., "A 1-mm 50 k-Pixel IT CCD Image Sensor for Miniature Camera System," IEEE Transactions on Electron Devices, Jan. 2000, 65-70, vol. 47, No. 1.

Jacques Duparré, et al., "Thin compound-eye camera," Applied Optics, May 20, 2005, pp. 2949-2956, vol. 44, No. 15.

Jun Tanida, et al., "Color imaging with an integrated compound imaging system," Optics Express, Sep. 8, 2003, 2019-2117, vol. 11, No. 18.

Jun Tanida, et al., "Thin observation module by bound optics (TOMBO): concept and experimental verification," Applied Optics, Apr. 10, 2001, 1806-1813, vol. 40, No. 11.

Ikeda, M., Sagawa, K., "Binocular color fusion limit," J. of the Optical Society of America, 69(2), 316-321, (Feb. 1979).

Dudley, D., Duncan, W. M., Slaughter, J., "Emerging digital miromirror device (DMD) applications," Proceedings of SPIE 4985, 14-25 (2003).

Hovis, J. K., "Review of Dichoptic Color Mixing," Optometry and Vision Science, 66(3), 181-190 (1998).

Lambooij, M., Ijsselsteijn, W., "Visual discomfort and visual fatigue of stereoscopic display: A review," J. of Imaging science and technology, 53(3), 030201 (2009).

DooHyun Lee and InSo Kweon, "A Novel Stereo Camera System by a Biprism," IEEE Transactions on Robotics and Automation, 16(5), 528-541, (Oct. 2000).

Mikko Kyto, Mikko Nuutinen, Pirkko Oittinen, "Method for measuring stereo camera depth accuracy based on stereoscopic vision," OAalto University School of Science and Technology, Department of Media Technology, Otaniementie 17, Espoo, Finland.

Qin, D., Takamatsu, M., Nakashima, Y., Qin, X., "Change of wavelength difference limit for binocular color fusion with wavelength and brightness of stimuli," J. of Light and Visual Environment, 30(1), 43-45 (2006).

Jung, Y. J., Sohn, H., Lee, S., Ro, Y. M., and Park, H. W., "Quantitative measurement of binocular color fusion limit for non-spectral colors.," Optics express, 19(8), 7325-7338 (2011).

Planar Systems Inc., "SD1710 Pruduct User's Guide," 1-12 (2005).

CRI Varispec, "Liquid Crystal Tuneable Filters," 1-12 (2005).

Avi Yaron, Mark Shechterman and Nadav Horesh, "Blur spot limitations in distal endoscope sensors," Proc. SPIE 5055, Stereoscopic Displays and Virtual Reality Systems XIII, 605509 (Jan. 27, 2006).

Researchers Work on Snake-Like 'Rescue Robots', downloaded on Apr. 20, 2006 from http://www.foxnew5.com/printer_friendly_story/O,3566, 192430,OO.htm.

NASA Infrared Camera Helps Surgeons Map Brain Turners, Jul. 15, 2004,downloaded on Apr. 24, 2006 from http://www.jpl.nasa.gov/news/news.cfm?release=20D4-183.

Fung et al., "A Case Study of 3D Stereoscopic VS. 20 Monoscopic Tele-Reality in . . . " IEEE/RSJ International Conference on Intelligent Robots and Systems, 2005, pp. 181-186.

Nain et al., "Three-Dimensional Nanoscale Manipulation and Manufacturing Using Proximal Probes: Controlled Pulling of Polymer . . . " IEEE Int Conf Rob Autom vol. 1,2004, pp. 434-439.

Lytle et al., Adapting a Teleoperated Device for Autonomous Control Using Three-Dimensional Positioning sensors: . . . Automation in Construction, vol. 13, 2004, pp. 101-118.

Mezouar et al., Robustness of Central Catadioptric Image-based Visual . . . • IEEE RSJ Int. Conf. IntelL Robots and Syst. IROS, vol. 2, Sep. 28-Oct. 2, 2004, Sendai, JP, pp. 1389-1394.

Murakami et al., "Automatic Insertion Work. Based on Visual Measurement and Contact Force Estimation" Proc IEEE Int Conf Rob Autom, vol. 4, May 2002, pp. 4167-4172.

Trivedi et al., "A Vision System for Robotic Inspection and Manipulation", DE90 005412, Univ of Tennessee, Revised Mar. 1989. pp. 1-12.

Nguyen et al., "30 Model Control of Image Processing" In JPL, California Inst. of Tech., Proceedings of the NASA Conference on Space Telerobotics, vol. 3, pp. 213-222 May 2000.

Stiel et af. Digital Flashing Tomosynthesis: A Promising Technique for Angiocardiographic ScreeningD IEEE Transactions on Medical Imaging, Jun. 1993, No. 2, NY, pp. 314-321.

Fritz, Eric., "High Speed Generation of Illumination Spectra for a Stereoscopic Endoscope", http://hdl.handle.net/2014/42272, NASA Undergraduate Student Research Program (USRP), Pasadena, California, Aug. 9, 2011, pp. 1-8, Retrieved from Internet: URL: http://trs-new.jpl.nasa.gov/dspace/bitstream/2014/42272/1/11-3811.pdf.

Ream, Allen, "Project report: reducing color rivalry in imagery for conjugated multiple bandpass filter based stereo endoscopy", http://hdl.handle.net/2014/42276, NASA Undergraduate Student Research Program (USRP), Pasadena, California, Aug. 2011, pp. 1-9, Retrieved from Internet: URL: http://trs-new.jpl.nasa.gov/dspace/bitstream/2014/42276/1/11-3803.pdf.

(56) References Cited

OTHER PUBLICATIONS

J.P. Rice et al., "Hyperspectral image compressive projection algorithm," SPIE vol. 7334 pp. 733414-1, , XP055046293, ISSN: 0277-786X, DOI: 10.1117/12.818844, (Apr. 27, 2009).

Sam Bae et al., "Toward a 3D endoscope minimally invasive surgery", SPIE Newsroom, Sep. 21, 2011, pp. 1-3, XP055046098, Doi: 10.1117/2.1201109.003810.

NASA's Jet Propulsion Laboratory et al: "Stereo Imaging Miniature Endoscope", Internet Citation, Jun. 30, 2011 (Jun. 30, 2011), pp. 6-7, XP002687431, Retrieved from the Internet: URL:http://ntrs.nasa.gov/archive/nasa/casi.ntrs.nasa.gov/20110012587_2011013131.pdf [retrieved on Dec. 3, 2012].

Ronald Korniski et al: "3D imaging with a single-aperture 3-mm objective lens: concept, fabrication, and test", Proceedings of SPIE, vol. 8144, Sep. 14, 2011 (Sep. 14, 2011), p. 812904, XP055046246, ISSN: 0277-786X, DOI: 10.1117/12.894110.

\* cited by examiner

ENDOSCOPE SYSTEM AND METHOD OF OPERATION THEREOF

This Application claims the benefit of U.S. Provisional Application No. 61/953,718, filed on Mar. 14, 2014, which is incorporated herein by reference in its entirety.

The present system relates to a surgical endoscopic microinstrument system and, more particularly, to surgical microinstruments with a camera for minimally-invasive surgical procedures and a method of operation thereof.

Typically, minimally-invasive endoscopic surgical procedures require several openings such as an opening for insertion of a viewing scope to view a region of interest (ROI) and a separate opening for insertion of a surgical tool such as a cutter, etc. Unfortunately, this necessitates additional surgical openings to access the ROI which is undesirable. Additionally, it is difficult for a surgeon to view a desired portion or view of the ROI while manipulating the surgical tool. Accordingly, the present systems and methods overcome deficiencies of the prior art endoscopes.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an endoscopic microinstrument, comprising a substantially rigid proximal body having first and second ends, a channel between the first and second ends; a substantially rigid distal end portion movably coupled to the body and having first and second ends; a tool located at the first end of the substantially rigid distal end portion and comprising first and second anvils; first and second handles coupled to the body, at least one of the handles further coupled to the tool and configured to control actuation of at least one of the first and second anvils; a camera coupled to, and situated to a side of, the substantially rigid distal end portion, the camera configured to obtain images of a region-of-interest; and an end portion controller coupled to the proximal body and configured to rotate the substantially rigid distal end portion relative to the substantially rigid proximal body to angulate and/or rotate the tool and the camera together or separately so that a line of sight of the camera is along a tool axis passing through the tool.

The endoscopic microinstrument may include a flexible portion which couples the substantially rigid distal end portion to the substantially rigid proximal body and is situated between the substantially rigid body and the substantially rigid end portion. Further, the end portion controller may be further configured to rotate the camera relative to the substantially rigid distal end portion. It should be understood that a device that is configure to perform a function is also able to actually perform the function. Thus for example, the controller which is configured to rotate the camera also actually rotates the camera, such by providing electronic signals (thought wired and/or wireless signal links) to actuators that rotate the camera and/or provide a force though mechanical cable connected between the controller and camera through couplings or other mechanical links.

The camera may be a wireless-type camera and may be situated outside of an exterior periphery of the substantially rigid distal end portion, where a longitudinal axis of a lens of the camera is parallel to and offset from a longitudinal axis of the substantially rigid distal end portion. Further, the camera may have a rotational mount to rotate the camera and/or the substantially rigid distal end portion about a longitudinal axis of the substantially rigid distal end portion independent of rotation of the tool, which may be any desired tool, such as a surgical gripper, a cutter, a coagulator, a dissector, a laser, laparoscope, and/or an ultrasonic tool including for ablation, pulverization, aspiration or otherwise.

The end portion controller may be further configured to rotate the camera relative to the distal end portion. Further, several controllers may be provided at the proximal end of the endoscopic microinstrument on and/or integral with the proximal body for example, such as a tool controller configured to control a function and/or a movement of the tool; a camera controller configured to control a function and/or a movement of the camera; and/or an end portion controller configured to control a movement of the distal end portion.

The camera may be configured to provide 2-dimensional (2D) and/or 3-dimensional (3D) images of the region-of-interest, where the endoscopic microinstrument may further comprise a rail-guide system for slidably receiving an imaging endoscope having a further camera and a further camera controller for controlling a function and/or a movement of the further camera to provide further 2D and/or 3D images of the region-of-interest. The camera may be extendable and retractable from a storage well of the distal end portion under control of one of the end portion controllers.

In another embodiment, an endoscopic microinstrument comprises a body having a channel; an end portion at a distal end of the endoscopic microinstrument, the end portion having a first end for being movably coupled to the body; a tool located at a second end of end portion distal from the first end of the end portion for being located at the distal end for manipulating a region-of-interest; a camera coupled to the end portion, the camera being configured to obtain images of the region-of-interest; and a plurality of controllers located at a proximate end of the endoscopic microinstrument, opposite the distal end, and being configured to control a function and/or a movement of the tool and/or the camera for synchronous movement together or independent movement.

The camera may be extendable and retractable from a storage well of the end portion under control of one of the plurality of controllers, which may include a tool controller configured to control a function and/or a movement of the tool; a first camera controller configured to control a function and/or a movement of the camera; a second camera controller configured to control extension and/or retraction of the camera from the storage well; and an end portion controller configured to control a movement of the end portion.

The camera may further comprise a rotational mount to rotate the camera or the distal end portion about a longitudinal axis of the end portion independent of rotation of the tool. Further, the camera may be a wireless-type camera and may be situated outside of an exterior periphery of the end portion for capturing and providing one of 2-dimensional (2D) and 3-dimensional (3D) images of the region-of-interest.

The present invention is explained in further detail in the following exemplary embodiments and with reference to the figures, where identical or similar elements are partly indicated by the same or similar reference numerals, and the features of various exemplary embodiments being combinable. In the drawings.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

Figure 1:
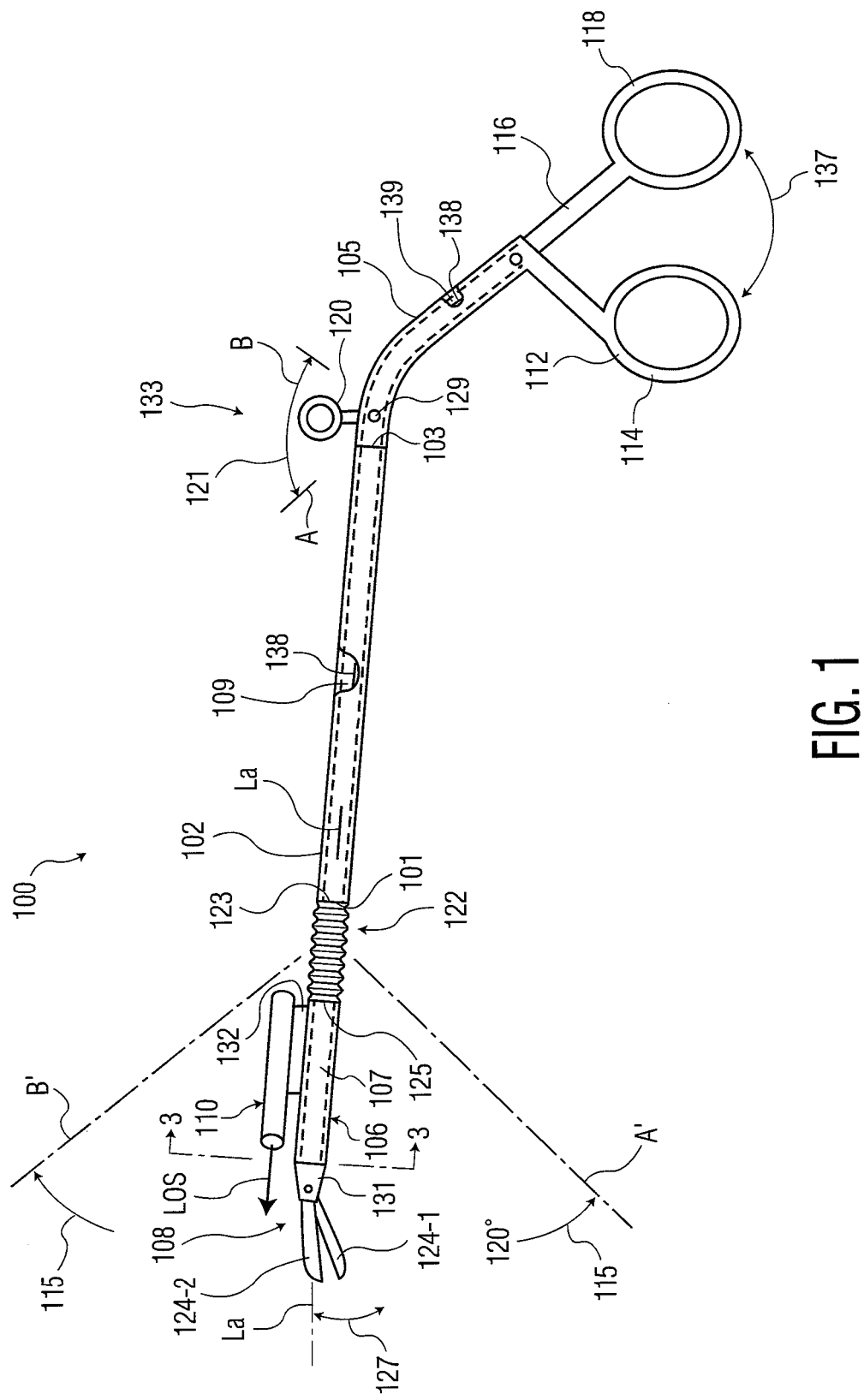
FIG. 1 shows a partially cutaway side view of a portion of a endoscopic microinstrument operating in accordance with embodiments of the present system.

FIG. 1 shows a partially cutaway side view of a portion of an endoscopic microinstrument 100 operating in accordance with embodiments of the present system. The endoscopic microinstrument 100 may include one or more of a body 102, a support portion 105, a flexible portion 122, a distal end portion 106, a tool 108, and a camera 110.

The body 102 may define a longitudinal axis La and may include proximal and distal ends 103 and 101, respectively. The body 102 may include a channel 109 situated between the proximal and distal ends 103 and 101, respectively, and which extends along the longitudinal axis La of the body 102. At least one control cable 138 may pass through the channel 109. Further, in accordance with some embodiments, the endoscope may be and/or include different types of instruments, such as without limitation, a laparoscope, an ultrasonic aspirator, a coagulator, a laser(s), a gripper, a cutter, a dissector, and/or other devices configured to perform desired operations at the ROI. Control of the various tools and/or cameras located at the tip or distal end of the instrument may be via wired or wireless connections to a controller located at the proximal end, where such controls include activation such as turning devices on/off or moving cutters to perform a scissor action, tip movement such as angulation of the tool(s) and camera(s), alone and/or in combination(s), that are located at the endoscopes tip or distal end to sweep in a desired 3D direction, e.g., up, down, right, left, rotation along instrument axis such as rotating a pair or scissors for cutting vertically and horizontally and in any other position therebetween.

The distal end portion 106 may be coupled to the body 102 using any suitable method so that it articulates, e.g., about at least a 120 degree arc (relative to a longitudinal axis La of the body 102) as illustrated by arrow 115 to provide side and/or rear views which are other than a front view provided by the camera when it is directed along the longitudinal axis La. Accordingly, the distal end portion 106 may be coupled to the body 102 using a flexible and/or elastic member such as the flexible portion 122 as will be discussed herein below. The distal end portion 106 may include a channel 107 through which the at least one control cable 138 may pass. The distal channel 107 communicates with the body channel 109 of the body 102, and may be of different size and/or shape to accommodate and/or go around objects, such as a camera storage bin or well (1676 shown in FIGS. 17-18) for storing the camera 110, in the case of a retractable/extendable camera as will be described in connection with the embodiments shown in FIGS. 12-18, where similar distal and body channels are provided.

The distal end portion 106 may further be coupled to the tool 108 and the camera 110 using any suitable method such as screwable mounts, friction fits, slip rings, etc. Additionally the tip may further rotate 360 degrees circumferentially around the La. The tip may be rotatable on its own, and/or may be rotated by rotating the entire endoscope which is typically located in a channel or lumen inserted in the incision opening and pushed toward the ROI, where various instruments may be inserted, retracted, and otherwise moved, e.g., rotated in this channel as necessary to perform a desired procedures. Such various hybrid instruments include the endoscopic microinstruments according to the present systems that include both at least one tool and at least one camera.

The tool 108 may include any suitable surgical tool such as a gripper, a cutter (shown), a dissector, an ultrasonic aspirator, a coagulator, a laser(s), etc. In accordance with some embodiments, the tool may include first and second anvils which may be configured for gripping, cutting, dissecting, coagulating, etc., as may be desired. For example, in accordance with some embodiments, the cutter may include first and second cutting anvils 124-1 and 124-2, respectively, (generally 124-x) at least one of which may articulate and/or rotate relative to the other (as illustrated by arrow 127) and which may be coupled to a base 131. The base 131 of the tool 108 may be coupled to the distal end portion 106 using any suitable method. In yet other embodiments, it is envisioned that at least one of the anvils (e.g., at least one of the first and second anvils 124-1 and 124-2, respectively may be fixedly attached to the base 131. Further, it is also envisioned that in accordance with some embodiments, the first and second anvils may be rotatably coupled to each other using a simple- or complex-type hinge assembly (e.g., providing simple or compound tool actions, respectively). Thus, at least one of the first and second anvils may be rotatably coupled to the base via the hinge assembly. Further, at least one of the first and second anvils 124-x which is movably coupled to the base 131 may be further coupled to the at least one control cable 138 so that the at least one control cable 138 may transfer an activation force to the anvil coupled thereto as will be described herein below. However, in yet other embodiments, an opening or closing assembly (e.g., for a compound action type tool) may be provided to open and/or close at least one of the first and second anvils 124-x.

The flexible portion 122 may include first and second ends 123 and 125, respectively. The first end 123 of the flexible portion 122 may be coupled to the distal end 101 of the body 102. The second end 123 of the flexible portion 122 may be coupled to the distal end portion 106. The flexible portion 122 may include at least one channel through which the at least one control cable 138 may pass. Further, the flexible portion 122 may include one or more simple or complex hinges (e.g., simple or compound hinges) which may provide for a desired amount of articulation and/or rotation of the second end 125 relative to the first end 123 of the flexible portion 122. In yet other embodiments, the flexible portion 122 may be formed integrally with at least one of the body 102 and the distal end portion 106. In yet other embodiments, it is envisioned that the flexible portion 122 may include an elastic hinge. Further, it is also envisioned that some embodiments may provide a biasing member to bias the flexible portion 122 in a desired direction and/or orientation relative to the body 102. Thus, for example, the biasing members may provide a returning mechanism to the distal end portion 106.

The support portion 105 may include a channel 109 through which the at least one control cable 138 may pass. The support portion 105 may be coupled to the body 102 using any suitable method or methods such as using a screwable mount. However, in yet other embodiments, it is envisioned that the support portion 105 may be coupled to the body 102 using any suitable method such as a bayonet-type mount, a friction fit, etc. However, in yet further embodiments, it is envisioned that the support portion 105 may be formed integrally with the body 102. The support portion 105 may include at least one gripping members such as first and second handles 112 and 116, respectively. The first and second handles 112 and 116 may each include an opening suitable for receiving at least one digit (e.g., finger) of a user, if desired, such as openings 114 and 118. At least one of the gripping members 112, 116 may be coupled to a corresponding one of the at least one control cable 138 so as to transfer a force thereto. This force may then be transferred to open or close at least one of the first and second anvils 124-1, 124-2 which is coupled to the at least one control cable 138. Thus, when a user opens or closes the first and second handles 112, 116, the first and second anvils 124-1, 124-2 may be opened or closed, respectively, or vice versa. Thus, a scissor action of the first and second handles 112 and 116, respectively (as shown by arrow 137), may be used to open and close the first and second anvils of the tool 108. This movement may provide a pinching force and/or a cutting force, depending upon a type of the tool 108 (e.g., scissors, pinchers, grippers, dissectors, etc.) provided.

The support portion 105 may further include an end portion controller 120 which may be movably (e.g., rotatably, slidably, etc.) mounted to the support portion 105 (e.g., using any suitable method such as a support pin) so as to control movement of the distal end portion 106 in 3-dimensions (3D). Accordingly, the end portion controller 120 may be coupled to the distal end portion 106 via a link such as at least one end portion control cable 134, 135 (shown in FIG. 2A) or the like which can transmit a force from the end portion controller 120 to the distal end portion 106 so as to deflect the distal end portion 106. For example, if the end portion controller 120 is moved along arrow 121 to be positioned in position A, the distal end portion 106 may be correspondingly positioned in position A', and if the end portion controller 120 is positioned in position B, the distal end portion 106 may be correspondingly positioned in position B'.

A friction and/or locking mechanism may be provided to hold the distal end portion 106 in a desired position during use. For example, in accordance with some embodiments, the end portion controller 120 may be depressed slightly (in the position shown by arrow 133) to unlock it and may be automatically locked when no longer depressed. Further, friction may be provided by a clutch (e.g., mechanical, electromechanical, etc.) if desired. Moreover, the at least one end portion control cable 134, 135 may include a casing which may be configured to engage the at least one end portion control cable 134, 135 to provide a desired amount of friction, if desired. It is also envisioned that a biasing member may provided to bias the end portion controller 120 and/or the distal end portion 106 coupled thereto to a desired position.

In one embodiment, a micro-motor may be provided to provide movement, such as articulation and/or rotation, of the flexible portion 120. For example, in addition to rotation, the flexible portion 120 may also be extended or retracted under the control of the controller 120 for more precise positioning of the tool 108 and/or camera 110. The motor may be operably coupled, e.g., via wire(s) and/or wireless communication link(s), to the controller 120 for controlling the motor to provide movement, articulation, and/or rotation of the flexible portion 120. Thus, mechanical linkages maybe replaced with electronic wired or wireless linkages as in 'fly by wire' systems using sensors, actuators, motors, servos and the like. For example, the motor may be located at the distal end 101 of the body 102, and may be any type of motor such as a continuous or stepper motor, for example.

The camera 110 may include any suitable imaging camera such as a video camera, a still camera, etc. which may obtain image information and transmit the image information to a controller of the endoscopic microinstrument 100 for further processing. The image information may include raw image information, processed image information, and/or metadata (e.g., time stamps, etc.). The camera includes a processor to process received images to form image signals or data and transmit the image signals or data to the system controller. The camera 110 may communicate with the system controller using any suitable wireless communication method. For example, the camera 110 may use a WiFi, Bluetooth™ communication methods or the like to transmit and/or receive information from a central controller and/or display for rendering. However, in yet other embodiments, a wired communication method such as using conductive wires and/or an optical fiber communication method may be used. The camera 110 may have a line-of-sight (LOS) which may extend in the direction of the longitudinal axis (La) of the body 102. The camera 110 may be fixedly or movably coupled to the distal end portion 106 via at least one camera support 132. However, in yet other embodiments, it is envisioned that the camera 110 may be coupled directly to the distal end portion 106. In yet other embodiments, a user interface (UI) may be provided to control orientation of the camera 110 relative to the distal end portion 106.

The camera 110 may include any suitable two-dimensional (2D) or three-dimensional (3D) image capture devices such as that shown and described in U.S. Pat. No. 7,601,119 to Shahinian, entitled "Remote Manipulator with Eyeballs," and issued on Oct. 13, 2009; U.S. Pat. No. 8,323,182 to Manohara, et al., entitled "Endoscope and System and Method of Operation thereof," and issued on Dec. 4, 2012; U.S. Patent Application Publication No. 2014/0088361 to Shahinian, et al., entitled "Multi-Angle Rear-Viewing Endoscope and Method of Operation thereof," and published on Mar. 27, 2014; U.S. Patent Application Publication No. 2014/0085420 to Shahinian, et al., entitled "Programmable Spectral Source and Design Tool for 3D Imaging Using Complementary Bandpass Filters," and published on Mach 27, 2014; and U.S. Patent Application Publication No. 2011/0115882 to Shahinian, et al., entitled "Stereo Imaging Miniature Endoscope with Single Imaging Chip and Conjugated Multi-Bandpass Filters," and published on May 19, 2011, the contents of each of which are incorporated herein by reference in their entirety. Further, the camera 110 may include an internal power supply, a memory, and/or at least one light source configured to provide illumination.

Figure 2A:
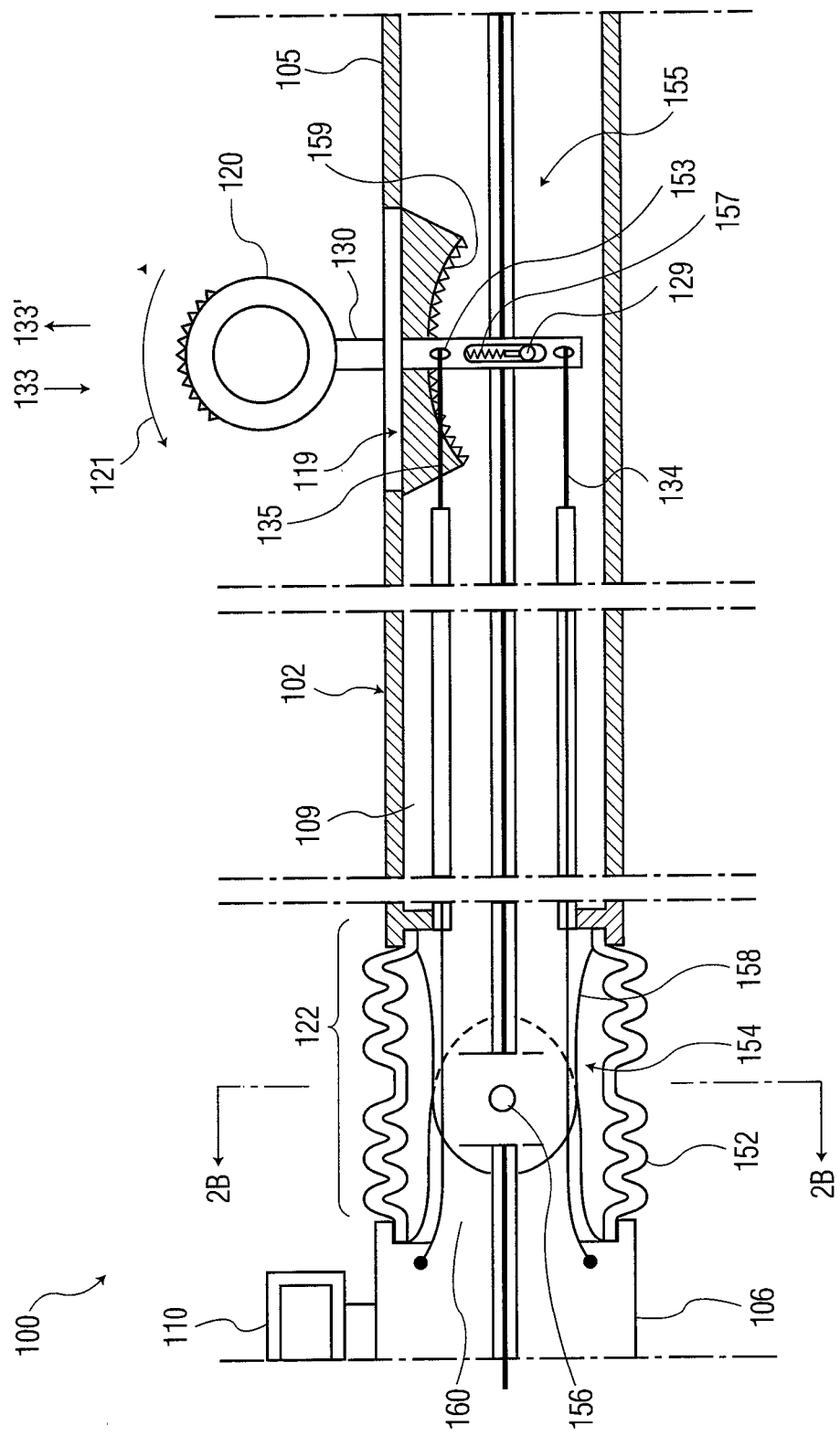
FIG. 2A shows a partially cutaway detailed side view of a portion of the endoscopic microinstrument operating in accordance with embodiments of the present system.

FIG. 2A shows a partially cutaway detailed side view of a portion of an endoscopic microinstrument 100 operating in accordance with embodiments of the present system. The flexible portion 122 may include an accordion-type cover 152 and at least one hinge 154. The at least one hinge 154 may include first and second hinge plates 158 and 160 coupled to each other by a hinge pin 156. Accordingly, the first and second hinge plates 158 and 160 may rotate relative to each other about the hinge pin 156. However, in yet other embodiments, it is envisioned that the flexible portion may include a plurality of hinge members. Regardless of type of hinge used, it is desirable that the hinge provide at least 120-180 degrees of motion, articulation and/or rotation. However, in yet other embodiments, other ranges are also envisioned.

The end portion controller 120 may have a shaft 130 that extends through an opening 119 (shown exaggerated in FIG. 2A for clarity) in the support portion 105 and may include a locking mechanism 155 provided to lock the end portion controller 120 in a desired position and may include any suitable locking mechanism, such as a biasing member 153, a toothed plate 159, an elongated slot 157, and a pin 129. The support pin 129 may extend through the elongated slot 157 so that the end portion controller 120 may move in the up-down directions shown by arrows 133, 133' (relative to the position of the end portion controller 120, such as relative the longitudinal axis La). However, the biasing member 153 may bias the end portion controller 120 in a direction shown by up arrow 133' to mesh the pin 129 into (teeth of) the toothed plate 159 so as to lock the pin 129 and thus, lock the end portion controller 120 in a desired (rotational) position along arrow 121. Depressing on the end portion controller 120 in the direction shown by down arrow 133 causes the end portion controller 120 to move down in the same direction and the pin 129 to disengage from the toothed plate 159. Accordingly, the end portion controller 120 may then be moved (e.g., rotatably along arrow 121) to a desired position. Then, when the end portion controller 120 is no longer depressed, it may be biased by the biasing member 153 (e.g., a coil spring) in the direction of up arrow 133' and locked in position by the pin 129 which engages the toothed plate 159.

The at least one end portion control cable may include first and second end portion control cables 134, 135, respectively, which may couple the end portion controller 120 to the end portion 106 so as to transfer a force from the end portion controller 120 to the end portion 106.

In other embodiments, the end portion controller 120 may operate as a joystick and moved in four directions along two perpendicular joystick axis, such as right, left, back and forward, to move the flexible portion 122 and thus the distal end portion 106 that includes both the tool 108 and camera 110 four directions, such as right, left, up and down. Alternatively or in addition, the joystick may move unconstrained about a joystick longitudinal passing through the joystick to move both the tool 108 and camera 110 in desired 3-dimensional directions following movements of the joystick. Alternatively or in addition, the end portion controller 120 may articulate and/or rotate about a shaft longitudinal axis of the shaft 130 to effectuate rotation by at least 120° and up to 180° of the flexible portion 122, and thus also of the distal end portion 106 that includes both the tool 108 and camera 110. The endoscopic microinstrument 100 may include for example, endoscopes, laparoscopes, etc.

Figure 2B:
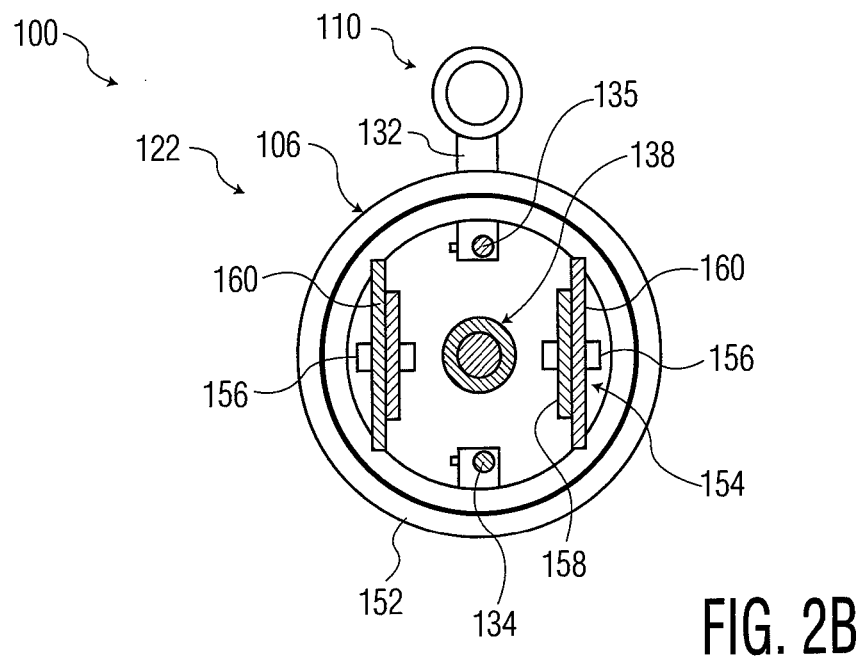
FIG. 2B shows a cross sectional view of a portion of the endoscopic microinstrument taken along lines 2B-2B of FIG. 2A in accordance with embodiments of the present system.

FIG. 2B shows a cross sectional view of a portion of the endoscopic microinstrument 100 taken along lines 2B-2B of FIG. 2A in accordance with embodiments of the present system. The hinge pin 154 may be split (as shown to provide room for passage of cables, etc.) or may be a single continuous hinge pin, if desired.

Figure 3:
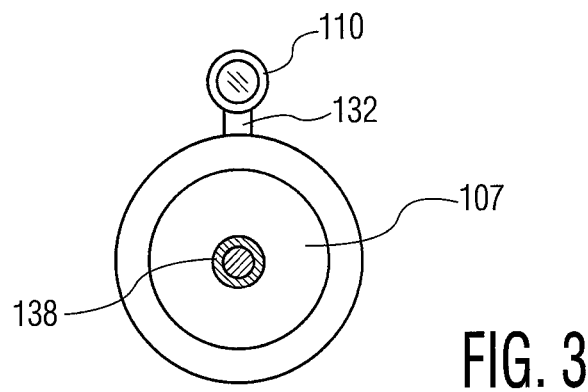
FIG. 3 shows a cross sectional view of a portion of the endoscopic microinstrument taken along lines 3-3 of FIG. 1 in accordance with embodiments of the present system.

FIG. 3 shows a cross sectional view of a portion of the endoscopic microinstrument 100 taken along lines 3-3 of FIG. 1 in accordance with embodiments of the present system. The at least one control cable 138 may pass through the channel 107.

Figure 4:
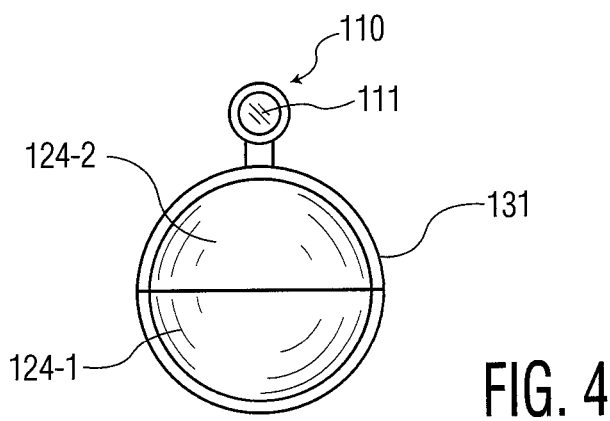
FIG. 4 shows an end view of a portion of the endoscopic microinstrument of FIG. 1 in accordance with embodiments of the present system.

FIG. 4 shows an end view of a portion of the endoscopic microinstrument 100 of FIG. 1 in accordance with embodiments of the present system. The first and second anvils 124-1 and 124-2, respectively, may be coupled to the base 131 (FIG. 1). The camera 110 may have at least one lens 111 or aperture through which an image may be captured of the ROI. In the case the camera 110 is a 3-D camera, then two openings or pupils are provided such as including a single lens dual aperture lens having filters such as the Conjugated Multi-Bandpass Filters (CMBFs) for 3D-visualization, such as described in U.S. Patent Application Publication Nos.

2011/0115882 and 2014/0085420 to Shahinian, et al., which are incorporated herein by reference in their entirety. It is further envisioned that the base 131 may include a cam to adjust the line-of-sight of the camera 110, if desired. Although the camera 110 is positioned at top of the distal end portion 106, in accordance with some embodiments, it may be positioned in various positions such as at the sides and/or bottom of the distal end portion 106, if desired.

Figure 5:
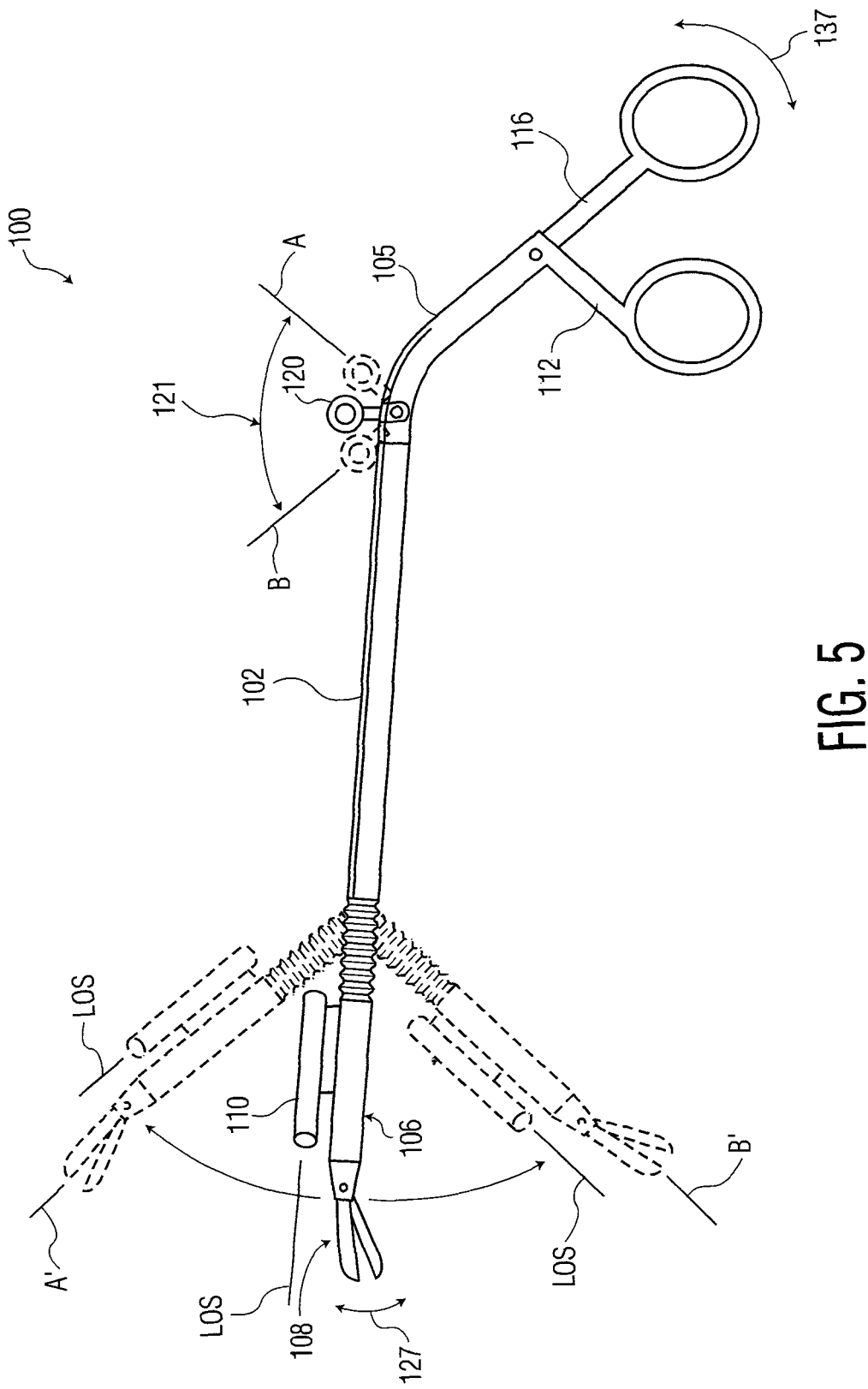
FIG. 5 shows a side view of a portion of the endoscopic microinstrument of FIG. 1 in accordance with embodiments of the present system.

FIG. 5 shows a side view of a portion of the endoscopic microinstrument 100 of FIG. 1 in accordance with embodiments of the present system. Moving the second handle 116 relative to the first handle 112 as illustrated by arrow 137 may open or close at least one of the anvils as illustrated by arrow 127. Accordingly, at least one of the first and second handles 112 and 116, respectively, may act as a trigger to open or close the tool 108. Further, moving the end portion controller 120 along arrow 121 into position indicated by A causes the end portion 106 to move to position A' and moving the end portion controller 120 into position indicated by B causes the end portion 106 to move to position B', as shown. However, in some embodiments, the movement may be reversed, if desired.

Figure 6:
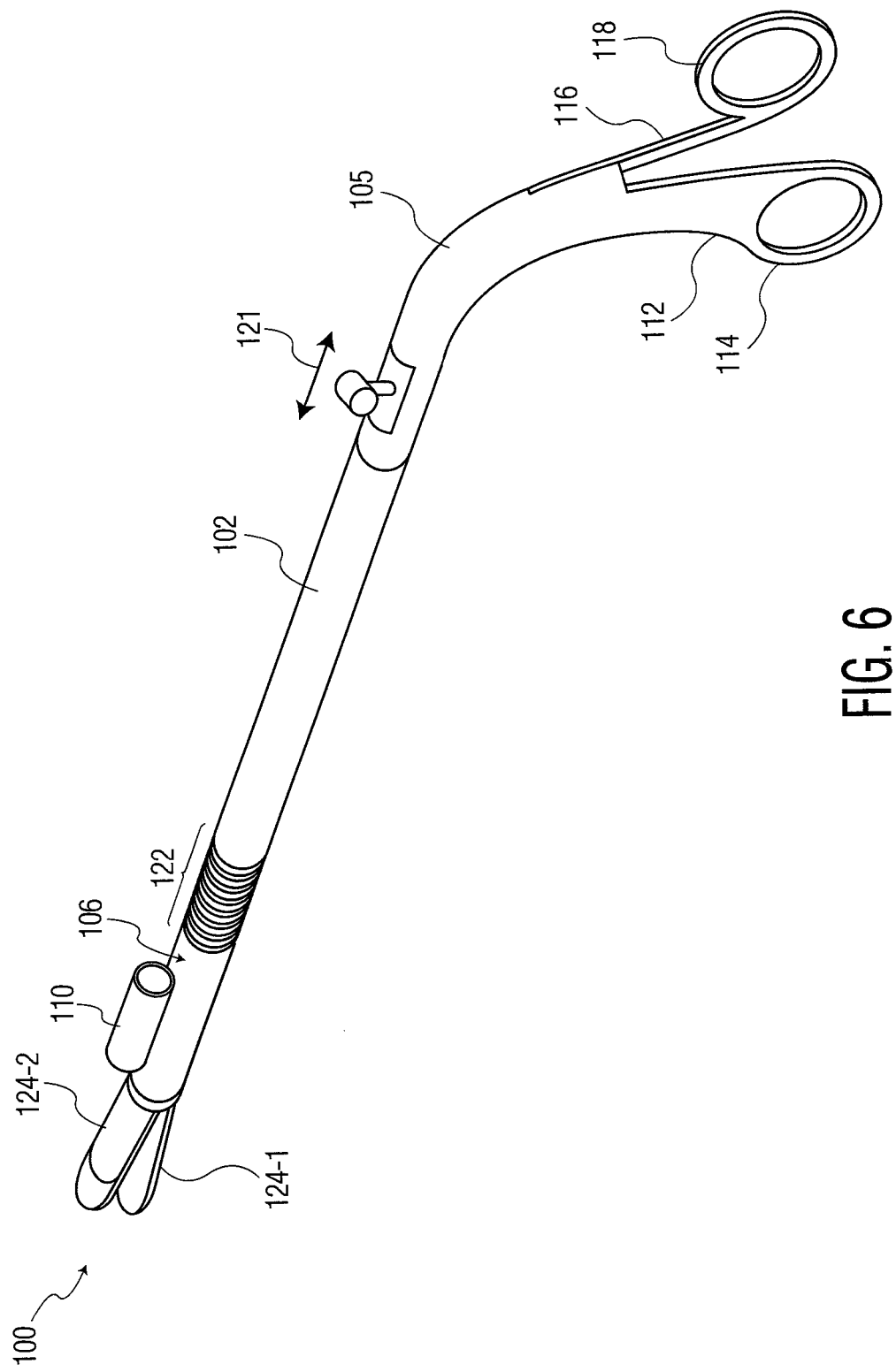
FIG. 6 shows a top perspective view of a portion of the endoscopic microinstrument of FIG. 1 in accordance with embodiments of the present system.

FIG. 6 shows a top perspective view of a portion of the endoscopic microinstrument 100 of FIG. 1 in accordance with embodiments of the present system.

Figure 7:
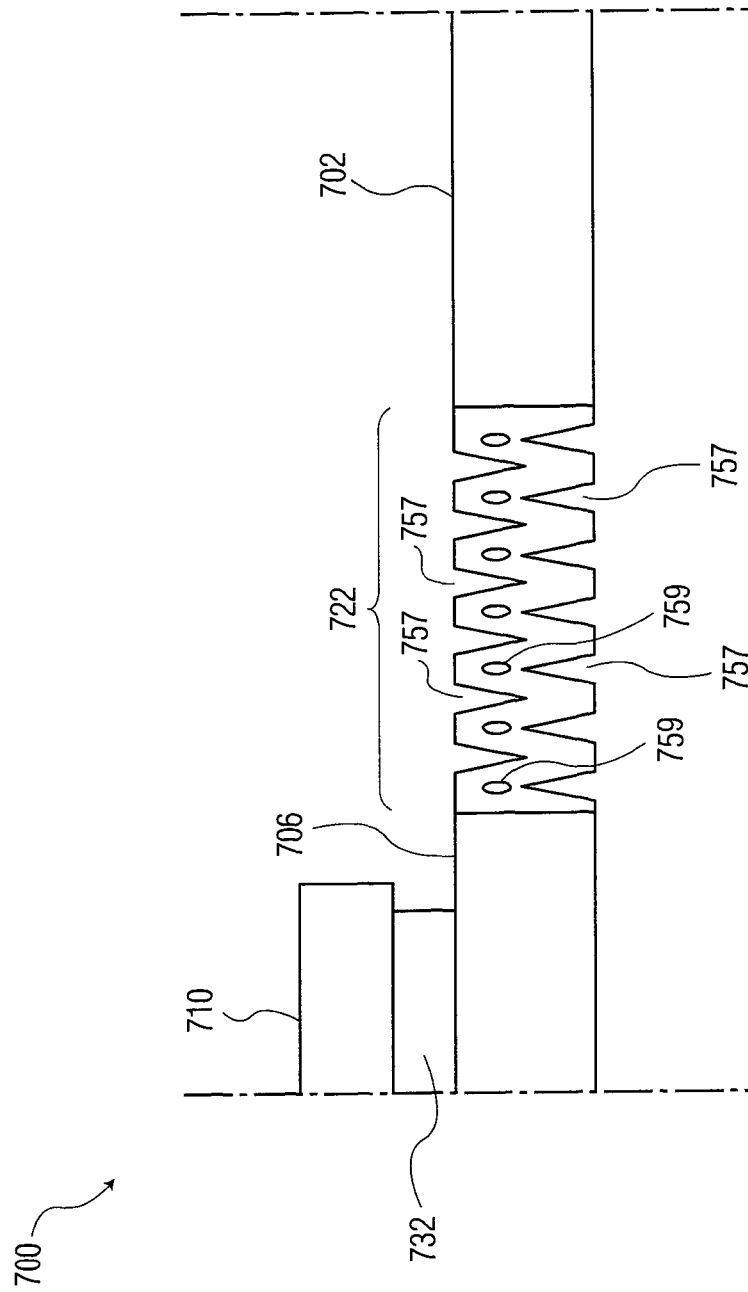
FIG. 7 shows a side view of a portion of an endoscopic microinstrument operating in accordance with embodiments of the present system.

FIG. 7 shows a side view of a portion of an endoscopic microinstrument 700, such as a laparoscope, operating in accordance with embodiments of the present system. The laparoscope 700 may be similar to the endoscopic microinstrument 100 and may include a body 702, a distal end portion 706 and a camera 710 supported on the distal end portion 706 by a camera support 732, which may be similar to the body 102, the distal end portion 106, and the camera 110. However, a flexible portion 722 which flexibly couples the distal end portion 706 to the body 702 may be formed integrally with the body 702 and may include a plurality of cutouts 757 and/or openings 759 which may provide for the flexing of the flexible portion 722 in a desired manner when subject to a force from the end portion controller 120. Further, the distal end portion 706 may be formed integrally with the body 702 and the flexible portion 722.

Figure 8:
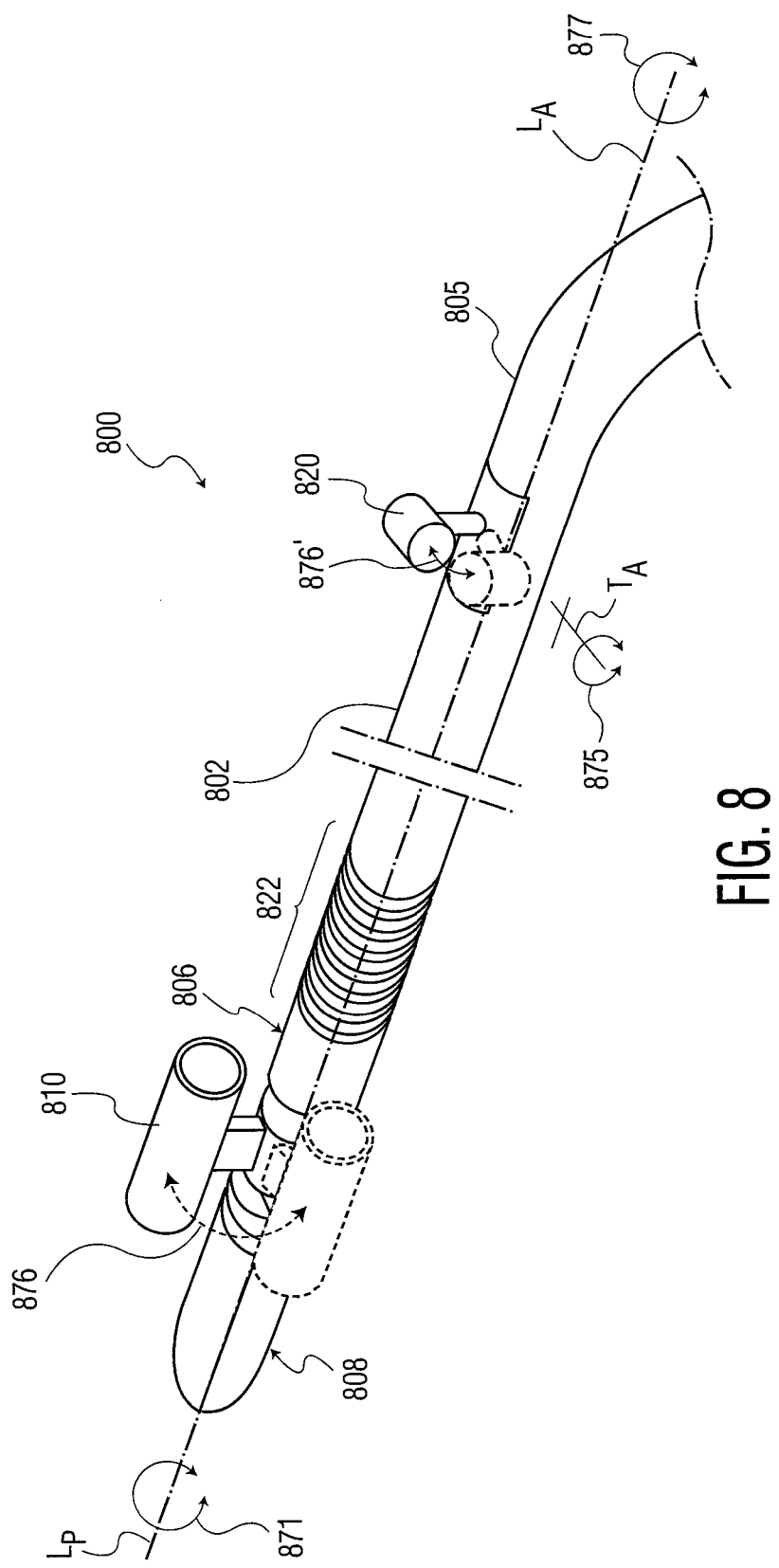
FIG. 8 shows a top perspective view of a portion of an endoscopic microinstrument in accordance with embodiments of the present system.

FIG. 8 shows a top perspective view of a portion of an endoscopic microinstrument 800 in accordance with embodiments of the present system. The endoscopic microinstrument 800 is essentially similar to the endoscopic microinstrument 100 of FIG. 1 and may include a body 802, a distal end portion 806, a flexible portion 822, a tool 808 (e.g., a surgical instrument or any other instrument that performs a designated function(s)), a camera 810, a support portion 805, and an end portion controller 120, which may be similar to the body 102, the distal end portion 106, the flexible portion 122, the tool 108 endoscopic microinstrument, the camera 110, the support portion 105, and the end portion controller 120 of 100 of FIG. 1. However, the distal end portion 806 may provide for rotational movement of the camera 810 and/or tool 808 about a longitudinal axis Lp of the distal end portion 806, as illustrated by arrow 871.

The camera 810 and tool 808 may be rotated together in unison or rotated independently/separately of each other. For example, the rotational movement of the camera 810 may be controlled by rotational movement of the end portion controller 820 about a longitudinal axis $L_A$ of the body 802, as shown by arrow 876'. The tool 808 may also be rotated independently of the camera rotation 876, such as using rotational couplers near the distal tool 808 and the proximal end portion controller 820 that rotate the tool 800 about the longitudinal axis, $L_P$ 871, or $L_A$ 877, similar to the rotational couplers 1390, 1391 that will be described in connection with the further embodiments below, such as shown in FIG. 12 for example.

Figure 12:
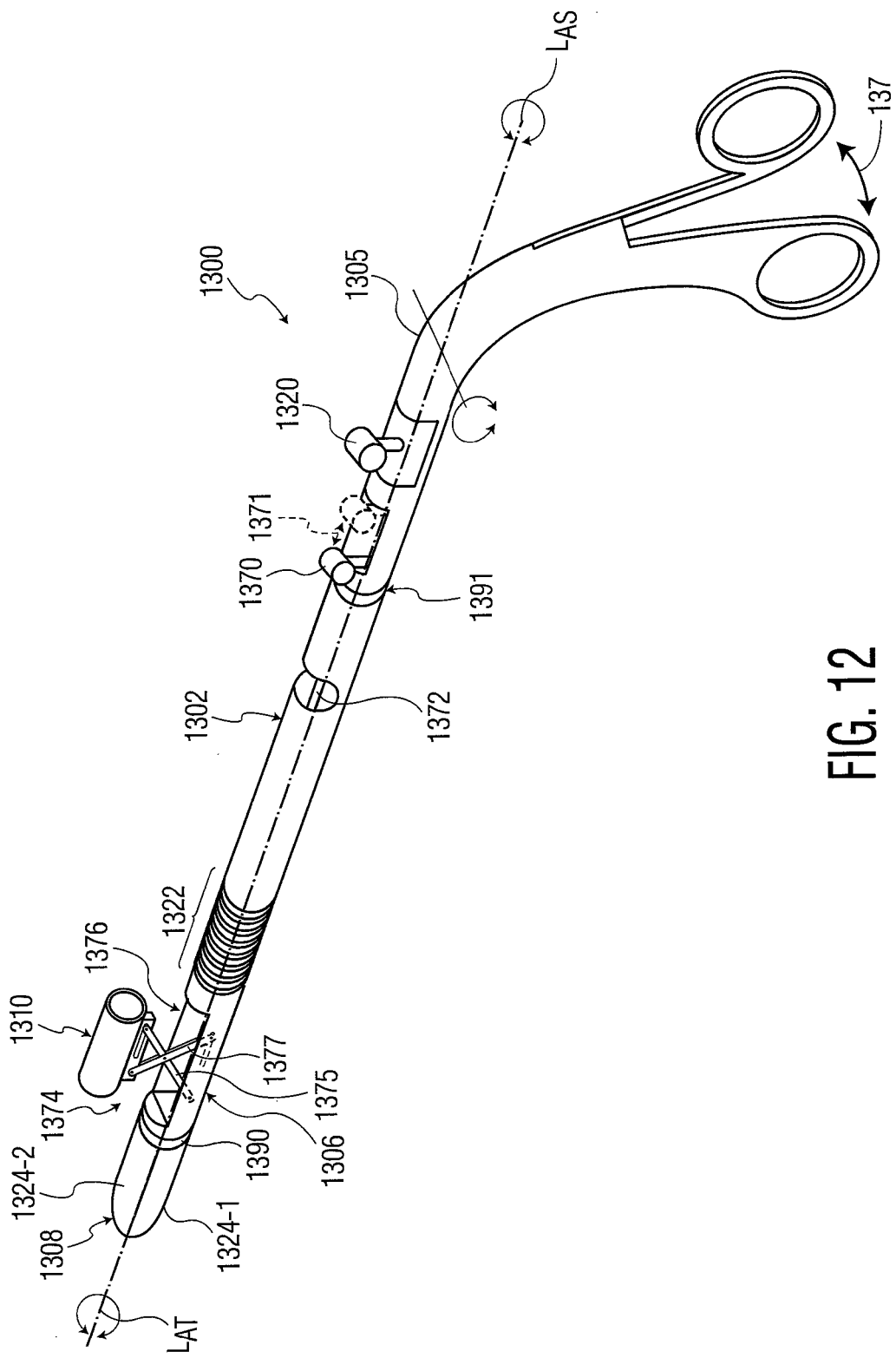
FIG. 12 shows a top perspective view of a portion of an endoscopic microinstrument including a scissor jack assembly in accordance with embodiments of the present system.

For example, the distal rotational coupler (e.g., shown as reference numeral 1390 in FIG. 12) may rotate in response to rotation of the proximal rotational coupler (e.g., shown as reference numeral 1391 in FIG. 12). Alternatively, the distal and proximal rotational couplers 1390, 1391 may each be independently controlled, such as in response to control signals from a UI or a moving joystick(s), for example.

Returning to FIG. 8, the end portion controller 820 may be moved about a transverse axis $T_A$ as illustrated by arrow 875, which motion may control movement of the distal end portion 806 similarly to that described with reference to the endoscopic microinstrument 100 of FIG. 1 and described above. For example, moving the end portion controller 820 along arrow 875 moves the distal end portion 806 by moving the flexible portion 822, e.g., to move between positions A' and B' shown in FIG. 1, in response to moving the end portion controller 820 along arrow 875 (FIG. 8), similar to arrow 121 in FIG. 1. Alternatively, rotation of the end portion controller 820 about its transverse axis $T_A$ (as shown by arrow 875) may cause the camera 810 to articulate and/or rotate about its longitudinal axis Lcp as illustrated by arrow 871 as will be described in connection with FIG. 10.

Further, the distal tip may rotationally move independently of the shaft and the camera. At least one control cable or link may be provided to translate movement of the end portion controller 820 parallel to the transverse axis $T_A$ (as illustrated by arrow 876') to a corresponding movement of the camera 810 relative to the distal end portion 806 as illustrated by arrow 876. Further, a locking mechanism may be provided to lock the camera into a desired position. It should be noted that the one or more control cables or links maybe mechanical (e.g., using cable, linkages, gears, pivots, levers, etc.) or electronic links, such as using wired or wireless communication among transceivers of control devices (e.g., end portion controller 820, retraction controller 1370, joystick, etc.) and controlled devices (e.g., camera 810 and or tool 808).

Figure 9:
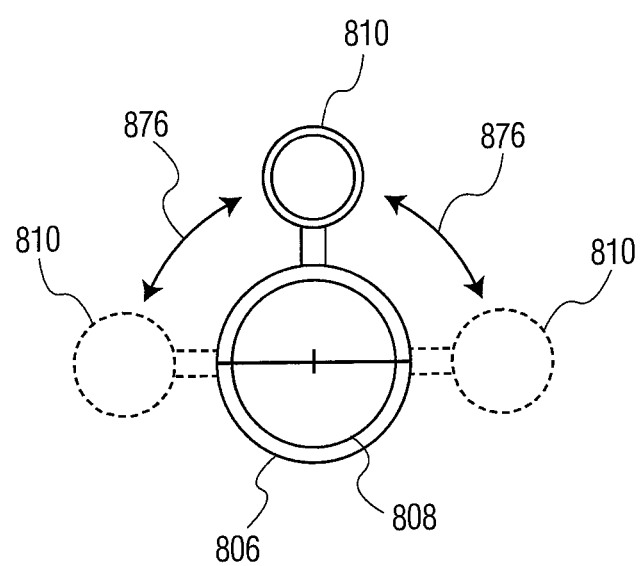
FIG. 9 shows an end view of a portion of the endoscopic microinstrument of FIG. 8 in accordance with embodiments of the present system.

FIG. 9 shows an end view of a portion of the endoscopic microinstrument 800 of FIG. 8 in accordance with embodiments of the present system. The camera 810 may be positioned relative to the distal end portion 806 and/or the tool 808 by moving the end portion controller 820 in a similar direction as illustrated by arrow 876.

Figure 10:
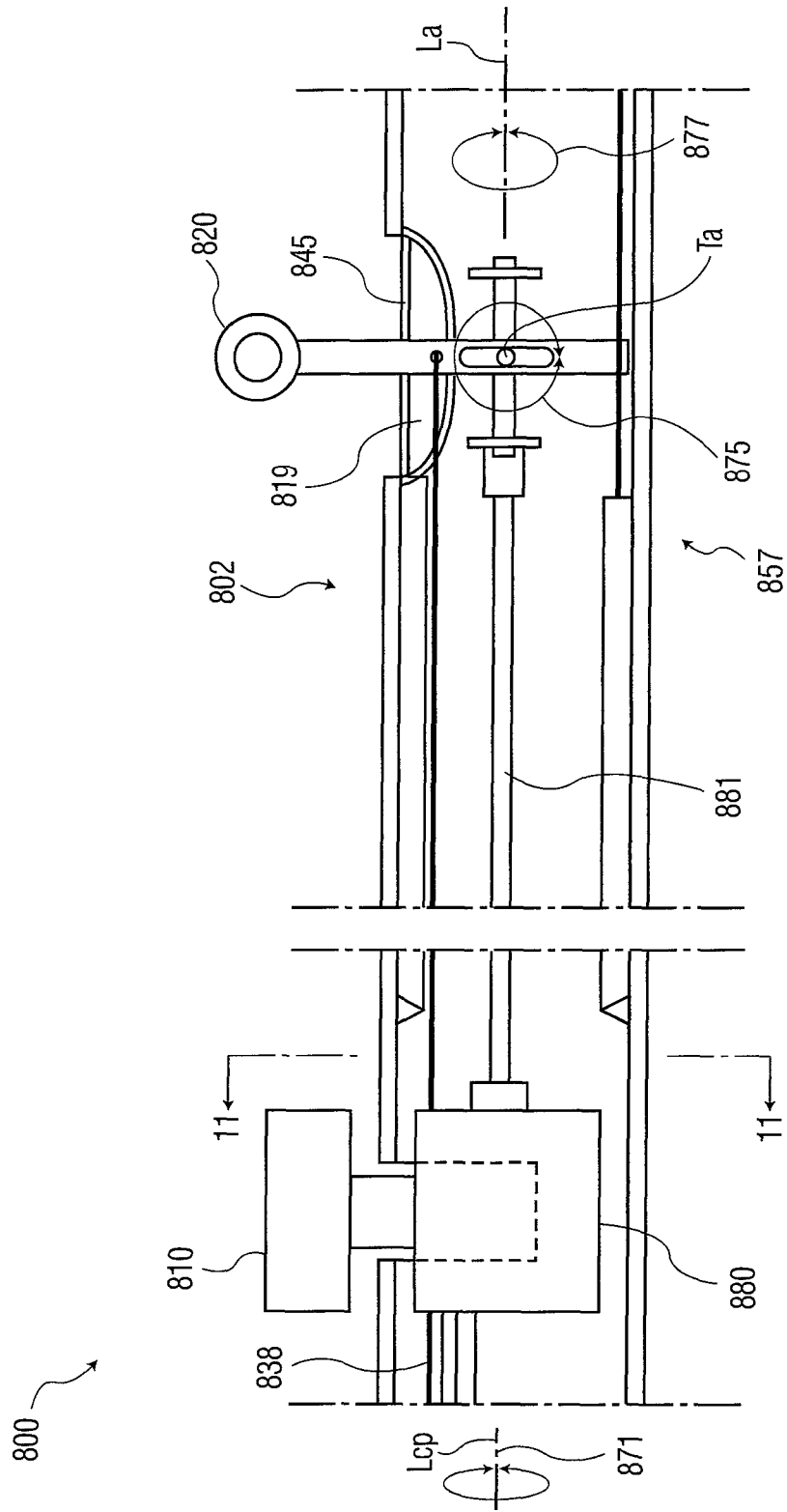
FIG. 10 shows a partially cutaway detailed side view of a portion of the endoscopic microinstrument operating in accordance with embodiments of the present system.

FIG. 10 shows a partially cutaway detailed side view of a portion of the endoscopic microinstrument 800 operating in accordance with embodiments of the present system. The end portion controller 820 may extend through an opening 819 in the support portion 805 and/or the body 802. A cover 845 may be provided to seal the opening 819, if desired. A dual motion linkage 857 may provide for motion of the end portion controller 820 about the longitudinal axis $L_A$ of the body 802 (which corresponds with the longitudinal axis $L_A$ of the at end portion controller 820 for the sake of clarity) as illustrate by arrow 877, and about the transverse axis $T_A$ of the end portion controller 820 as illustrated by arrow 875. The motion of the end portion controller 820 about the longitudinal axis $L_A$ of the body 802 may be translated to movement of the end portion 806 as discussed with respect to the laparoscope 100 of FIG. 1. However, the motion of the end portion controller 820 about its transverse axis $T_A$ (as shown by arrow 875) may cause the camera 810 to articulate and/or rotate about its longitudinal axis Lcp as illustrated by arrow 871. This latter motion may be accomplished by transferring a force from the end portion controller 820 to the camera 810 via a linkage 881 (e.g., a cable) which coupled the camera 110 to the end portion controller 820. Further, the camera 810 may include a rotational support such as a cylinder 880 which may slidably and rotationally engage an interior portion of the end portion 806 so as to locate the camera 810 in a desired rotational position about the camera longitudinal axis Lcp. Control linkages and/or cables may pass through the cylinder 880. At least one control cable 838 (only a portion of which is shown for the sake of clarity) may pass through a channel of the body 802 and/or end portion 806 and may be similar to the at least one control cable 138 and may be operative to control operation of a tool of the endoscopic microinstrument 800.

Figure 11:
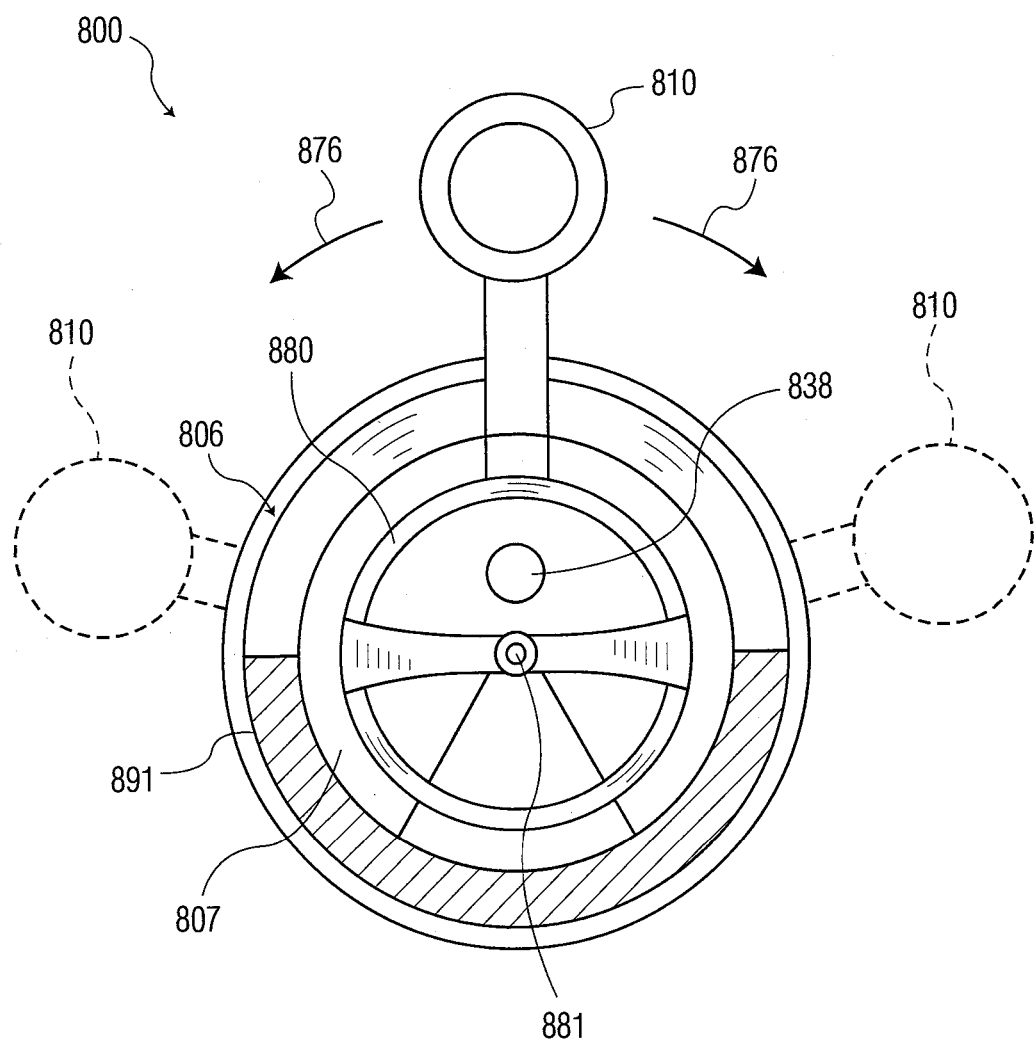
FIG. 11 shows a cross sectional view of a portion of the endoscopic microinstrument taken along lines 11-11 of FIG. 10 in accordance with embodiments of the present system.

FIG. 11 shows a cross sectional view of a portion of the endoscopic microinstrument 800 taken along lines 11-11 of FIG. 10 in accordance with embodiments of the present system. The at least one control cable 838 may pass through the channel 807 of the distal end portion 806.

In accordance with other embodiments, the camera may be attached to the distal end portion using hook-loop fasteners such as snap ties, Velcro™, and the like. Further, more than one tool may be coupled simultaneously to the distal end portion for providing different functions, such as cutters for cutting, lasers or bipolar electricity for cauterizing, ultrasonic aspiration for example.

Further, the endoscopic microinstrument 800 may include a light source and/or light guide (e.g., a light ring 891 which may be placed in the vicinity of the tool 808 and/or camera 810 to provide illumination of a working area) to provide illumination for the camera 810. Moreover, a power source such as an internal and/or external power source, e.g., a battery which may be rechargeable, may be provided to operate various portions of the endoscopic microinstrument such as the camera 810, the light source, communication links, the coagulator, lasers, etc. The light source may be provided at the proximal end 103 of the body 102 where a light guide, e.g., fiber optic cable, may be connected between the proximal light source and distal light ring 891, where the light ring 891 is a termination of the light guide outcoupling the light traveling in the light guide for exit from the light ring 891.

In accordance with yet other embodiments, the camera may be stored within a camera well of the distal end portion and may extend out of the camera well (e.g., pop up) for use, and retract within the camera well to minimize size for or during insertion through a minimally-invasive surgical opening and retrieval from the surgical opening as may be desired. This may reduce the diameter of the endoscopic microinstrument of the present system for insertion through the minimally invasive surgical opening and/or channel which may be pre-inserted in the opening to the ROI, which desired instruments including the present endoscopic microinstrument may be inserted and moved in the channel. For example, during minimally invasive brain surgery, no channel is used where the endoscopic microinstrument and a further instrument(s), as necessary, are inserted through an opening made in the skull. By contrast, in other types of surgery, a channel in inserted in an opening or incision, where the channel may extend up to the ROI and where the present endoscopic microinstrument and further instrument, as necessary, are inserted through the channel.

Illustratively, the surgical opening and/or channel may have a diameter of about 12 mm-15 mm, the camera may have a diameter of about 4 mm with a light ring around the camera, and less than 3 mm (such as 2.89 mm) without a light ring. Thus there is at least 8 mm-11 mm left for other instruments, including the hybrid instrument that the camera attaches to in accordance with the present endoscopic microinstruments and systems. If the instrument has its own light ring for illumination, then there is no need for the camera to also have a light ring. Of course, in the embodiment where the camera is retractable inside the instrument (see FIG. 15), more space is available in the channel for insertion of other instruments. For example, a retraction assembly such as a scissor jack assembly, a parallel arm jack assembly or non-parallel (e.g., short-long) arm jack assembly, a rotatable assembly, or the like may position the camera to a desired location from storage within a camera storage area.

In a further embodiment, an imaging endoscope having only the camera is inserted in the opening and/or channel/cannula and located at the 12 o'clock position, and below the imaging endoscope, the hybrid endoscopic microinstrument as described, having a combination of both a tool and its own camera, is inserted. In this case, as the hybrid endoscopic microinstrument has its own light ring for providing illumination of the ROI, the camera of the imaging endoscope does not need a light ring, thus further reducing its size, such as from 4 mm to less than 3 mm in diameter, for example.

The imaging endoscope and the hybrid endoscopic microinstrument may be coupleable together, such as through a guide/rail system, where one of the imaging endoscope or the hybrid endoscopic microinstrument, e.g., the imaging endoscope, has a guide and the other of the imaging endoscope or hybrid endoscopic microinstrument, e.g., the hybrid endoscopic microinstrument, has a complementary rail that fits in the guide of the imaging endoscope and slides along the guide until the flexible part of the hybrid endoscopic microinstrument reaches and extends past the guide at the distal end of the imaging endoscope so that the flexible part allows movement of the combination of both tool and camera of the hybrid endoscopic microinstrument, as described, for viewing and performing a desired operation, such as cutting, ablation via heat, radio frequency (RF) or laser, aspiration, ultrasound agitation, etc.

It should be understand that the locations of guide and rail may be variable where the imaging endoscope having one of the guide and rail slides along the other of the guide and rail located at a side or bottom of the hybrid endoscopic microinstrument, instead of being located at a top of the endoscopic microinstrument. Similarly, the locations of the imaging endoscope and the hybrid endoscopic microinstrument may be variable, such as having the hybrid endoscopic microinstrument being above, instead of below, the imaging endoscope. Similarly, in the hybrid endoscopic microinstrument including the combination of tool and camera, the number and locations of the tool(s) and camera(s) may vary, such as having one or more cameras located (or extended from) below or at side(s) of the tool(s), instead of being located, or extended from, above the tool. Thus, the imaging device including a camera, optics, filters, detectors and processors, maybe hanging on the underside of the hybrid endoscopic microinstrument, including having the camera storage at this underside.

The two imaging devices, such as the stand-alone camera-1 on the imaging endoscope and camera-2 on the hybrid endoscopic microinstrument that includes a combination tool and camera, maybe be 2D and/or 3D cameras in any combination, such as to provide 2D or 3D birds-eye or panoramic reference images using camera-1 and to provide 2D or 3D working images using camera-2 that are more detailed than the panoramic reference images and/or more directed towards or more focused on the ROI where the tool is to be used.

The imaging device(s) at the distal end of the imaging endoscope and/or the hybrid endoscopic microinstrument may include optics, detectors, filters such as the Conjugated Multi-Bandpass Filters (CMBFs) for 3D-visualization, CMOS or CCD detectors and processors to process images detected by the detectors and provide video signals to a display(s) or monitor(s) for 2D and/or 3D display of images captured by the imaging device(s) for viewing by a viewer(s). Imaging devices for capturing 3D images include those having CMBFs such as described in U.S. Patent Application Publication Nos. 2011/0115882 and 2014/0085420 to Shahinian et al., which are incorporated herein by reference in their entirety.

During a surgical procedure, the imaging endoscope may be fixed to provide a birds-eye or panoramic reference view, while the camera and tool combination of the hybrid endoscopic microinstrument are moved in a 3-dimensional (3D) direction, e.g., up, down, right left, front, back. Both images from the camera of the imaging endoscope and the camera of the endoscopic microinstrument are displayed on a screen in any desired format, such as a picture-in-picture format (PIP), for example, where the birds-eye or panoramic reference view provided by the camera of the imaging endoscope shows the tool or the combination of the tool and camera of the endoscopic microinstrument.

Figure 13:
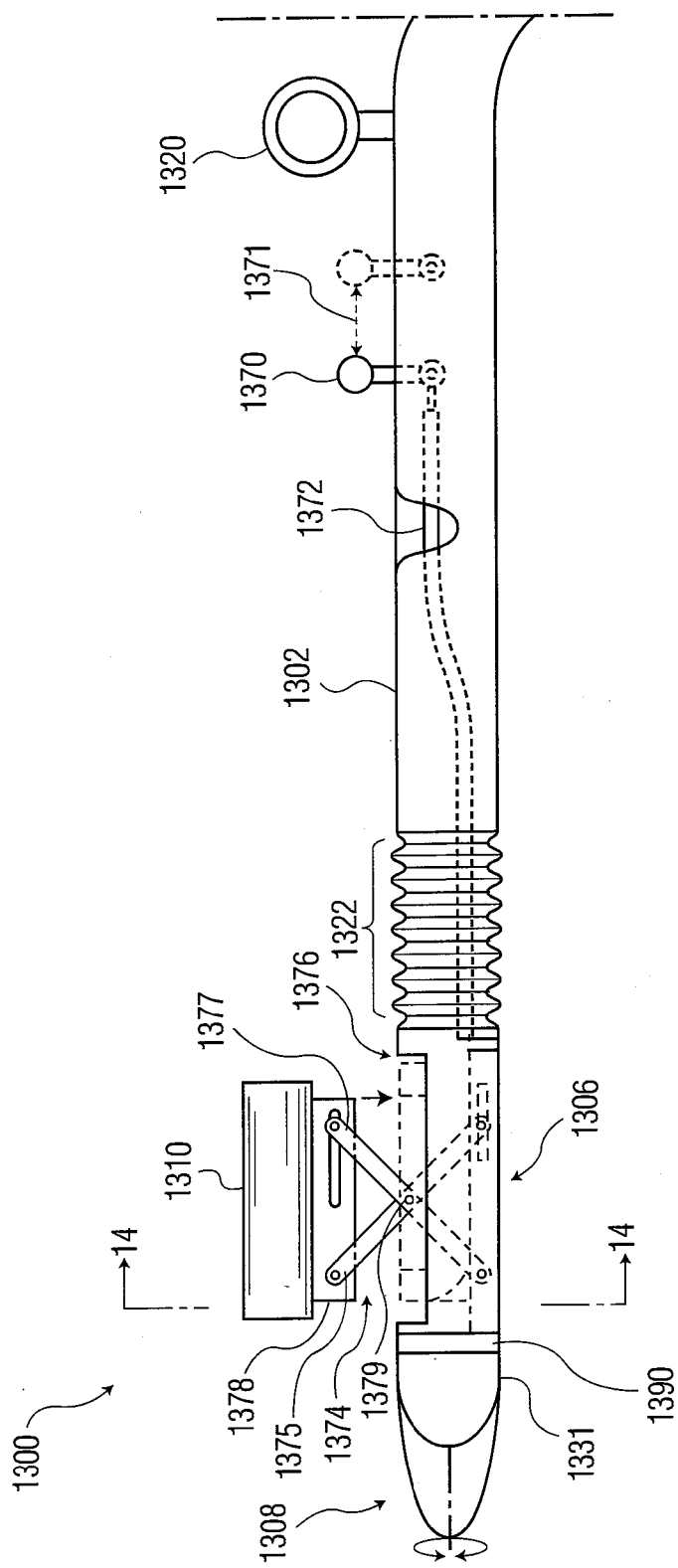
FIG. 13 shows a side view of a portion of an endoscopic microinstrument of FIG. 12 in accordance with embodiments of the present system.

With regard to a scissor jack assembly, FIG. 12 shows a top perspective view of a portion of an endoscopic microinstrument 1300 including a scissor jack assembly 1374 in accordance with embodiments of the present system. The endoscopic microinstrument 1300 may be essentially similar to the endoscopic microinstrument 100 of FIG. 1 and may include a body 1302, a distal end portion 1306, a flexible portion 1322, a tool 1308, a camera 1310, a support portion 1305, and an end portion controller 1320, which may be similar to the body 102, the distal end portion 106, the flexible portion 122, the tool 108, the camera 110, the support portion 105, and the end portion controller 120, respectively, of the endoscopic microinstrument 100 of FIG. 1. However, the distal end portion 1306 may include a scissor jack assembly 1374 which may position the camera 1310 into a desired location for storage within a camera storage well 1376 within the distal end portion 1306. A retraction control cable 1372 may couple a retraction controller 1370 (which may be located on the body portion 1302 or support portion 1305, as may be desired) to the scissor jack assembly 1374 to controllably extend or retract the camera 1310 from the camera storage well 1376 by sliding the retraction controller 1370 as shown by arrow 1371. The scissor jack assembly 1374 may include at least two support arms such as first and second support arms 1375 and 1377, respectively, which may be pivotably coupled to each other at pivot 1379. As shown in FIG. 13, one end of the first support arms 1375 may be pivotably coupled to a camera base 1378 by a pin, while the other end has a pin for pivotably sliding through a slot in the distal end portion 1306. Similarly, one end of the second support arms 1377 may be pivotably coupled to the distal end portion 1306 by a pin, while the other end has a pin for pivotally sliding through a slot in the camera base 1378. Alternately or in addition, both ends of both first and second support arms 1375 and 1377 may have pins for pivotally sliding through slots in the distal end portion 1306 and the camera base 1378.

FIG. 13 shows a side view of a portion of an endoscopic microinstrument 1300 of FIG. 12 in accordance with embodiments of the present system. As shown in FIGS. 12-13, the tool 1308 may include a base 1331 which may include a rotational coupler 1390 which may provide for the tool 1308, such as the anvils 1324-1 and 1324-2 (generally 1324-x) to rotate about a longitudinal axis ($L_{AT}$) of the tool 1308 while the body portion 1302 may remain rotationally stationary, thus providing for rotation of the tool 1308 which is independent from the rotation of the optics or visualization system collectively referred to as the camera 1310. Similarly, the support portion 1305 may include a rotational coupler 1391 which allows the support portion 1305 to rotate about a longitudinal axis ($L_{AS}$) of the support portion 1305 while the body portion 1302 may remain rotationally stationary about its longitudinal axis $L_{AS}$, when the distal and proximal couplers 1390, 1391 are in an uncoupled state. In a coupled state, the distal and proximal couplers 1390, 1391 are coupled to each other, such as via electronics or mechanical linkage systems including, e.g., signal wires and/or mechanical cables coupled to couplings, actuators, motors, sensors, and/or controllers for wired or wireless communication between the distal and proximal couplers 1390, 1391, such as for synchronous operation of the two couplers 1390, 1391.

For example, rotation of the proximate coupler 1391 causes rotation of the distal coupler 1390, wither by the same amount or by different amounts, such as using gears and/or actuators controlled by control signals to provide desired fine or course rotation of the distal coupler 1390 in response to an rotation of the proximal coupler 1391, whose rotation granularity may be adjustable, such as by control signals from an input source, e.g., knob, button, user interface to provide fine or course turning of the proximal coupler 1390 to rotate the tool 1308. For fine turning, a high rotation ratio value, e.g., 10 or higher, is provided for a ratio of rotation of the distal coupler 1391 to the rotation of the proximal coupler 1390, where a 100° rotation of the proximal coupler 1390, rotates the distal coupler 1390 by 10°, for example. For course turning, the ratio value maybe less than 9, for example. For the sake of clarity, $L_{AT}$ and $L_{AS}$ may correspond with the $L_A$. The support portion 1305 may then be rotationally coupled to the tool 1308 by at least one rotational link (e.g., a cable, etc.) so that rotation of the support portion 1305 relative to the body 1302 may correspondingly rotate the anvils 1324-x or tip of the tool relative to the body 1302. Rotating the anvils 1324-x or tip (e.g., work portion) of the tool 1308 may be performed to obtain a desired orientation of the tool 1308 relative to a work area.

Alternatively, instead of the distal rotational coupler 1390 rotating in response to rotation of the proximal rotational coupler 1391, each of the distal and proximal rotational couplers 1390, 1390 may be independently controlled, such as in response to control signals from a UI or a moving joystick, for example, such as one more of the end portion controller(s). Illustratively, a tool joystick-1 may control rotation of the distal coupler 1390 to rotate the tool 1308 about the tool longitudinal axis $L_{AT}$ and/or move the distal end to any desired position, such as positions A', B' shown in FIG. 1, while another tool joystick-2 may control movement of the anvils 1324-1, 1324-2, e.g., to open and close them for scissor cutting or snipping action. It should be noted that one or more physical joysticks may be provided that can be configured by a processor to operate in different modes, under the control of the processor. For example, instead of having two physical joysticks, one physical joystick may be provided that has a first mode to operate as joystick-1, and a second mode to operate as joystick-2 of the above described example.

Figure 14:
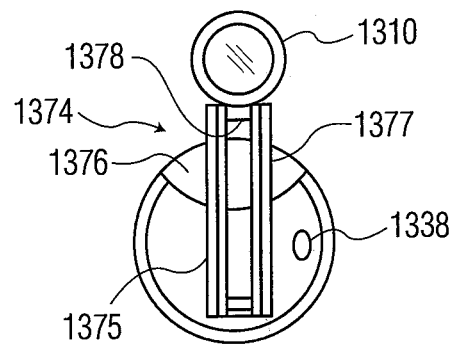
FIG. 14 shows a cross sectional view of a portion of the endoscopic microinstrument taken along lines 14-14 of FIG. 13 in an extended camera mode in accordance with embodiments of the present system.

FIG. 14 shows a cross sectional view of a portion of the endoscopic microinstrument taken along lines 14-14 of FIG.

13 in accordance with embodiments of the present system. The camera 1310 is shown in the extended position (e.g., to capture image information). The endoscopic microinstrument may include control and/or data cables such as at least one cable 1338 which may be similar to the at least one cable 138.

Figure 15:
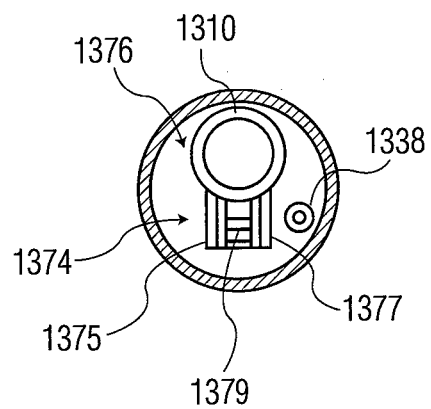
FIG. 15 shows a cross sectional view of a portion of the endoscopic microinstrument taken along lines 14-14 of FIG. 13 in a refracted camera mode in accordance with embodiments of the present system.

FIG. 15 shows a cross sectional view of a portion of the endoscopic microinstrument taken along lines 14-14 of FIG. 13 in accordance with embodiments of the present system. The camera 1310 is shown in the retracted position.

Figure 16:
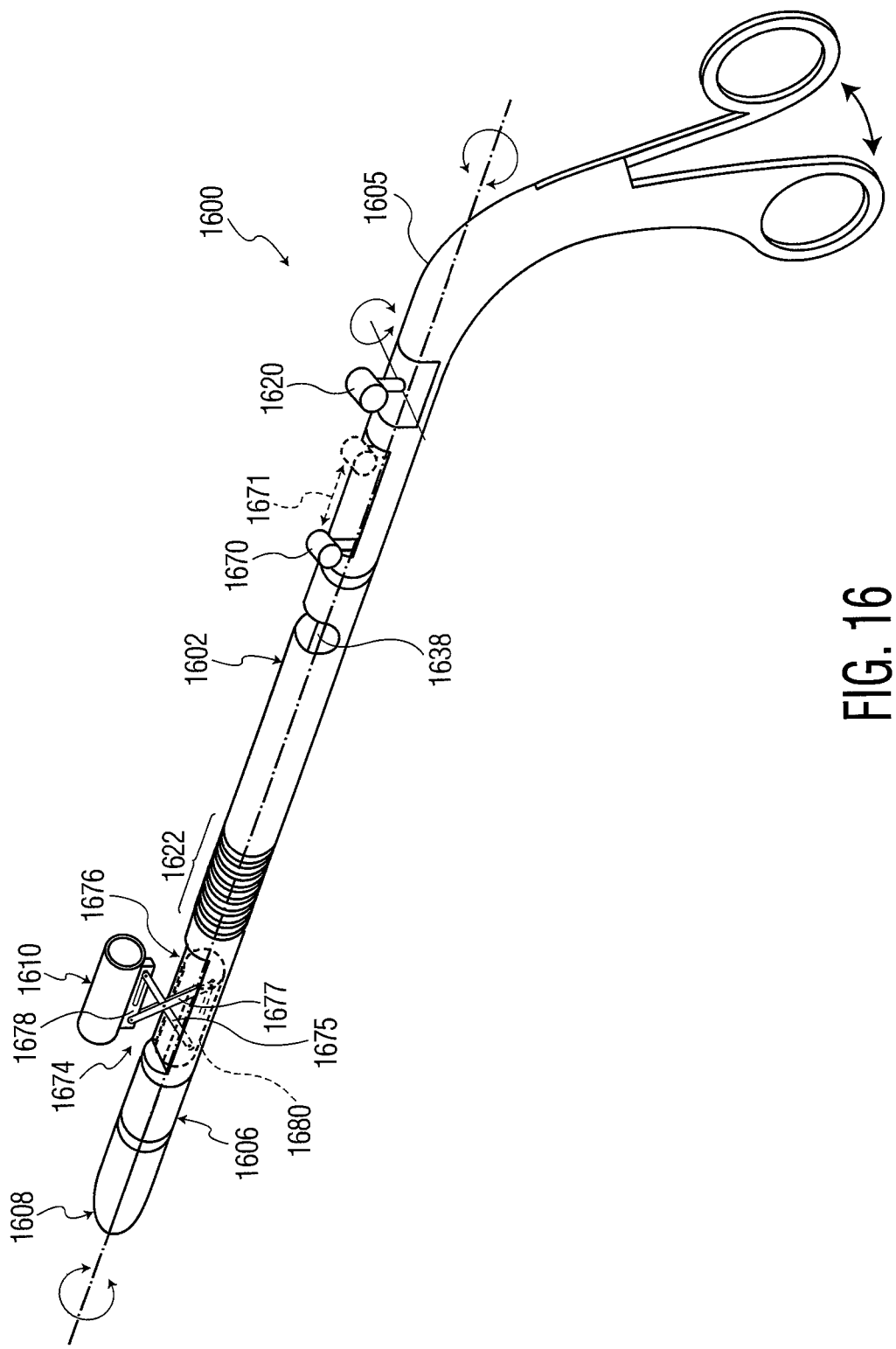
FIG. 16 shows a top perspective view of a portion of an endoscopic microinstrument including a scissor jack assembly in accordance with embodiments of the present system.

FIG. 16 shows a top perspective view of a portion of an endoscopic microinstrument 1600 including a scissor jack assembly 1674 in accordance with embodiments of the present system. The endoscopic microinstrument 1600 may be essentially similar to the endoscopic microinstrument 800 of FIG. 8 and may include a body 1602, a distal end portion 1606, a flexible portion 1622, a tool 1608, a camera 1610, a support portion 1605, a cylinder 1680, and an end portion controller 1620, which may be similar to the body 802, the distal end portion 806, the flexible portion 822, the tool 808, the camera 810, the support portion 805, the cylinder 880, and the end portion controller 820, respectively, of the endoscopic microinstrument 800 of FIG. 8. However, the support portion 1605 may include a scissor jack assembly 1674 which may position the camera 1610 into a desired location from storage within a camera storage well 1676 within the cylinder 1680 of the end portion 1306. A retraction control cable 1672 may couple a retraction controller 1670 (which may be located on the body portion 1602 or support portion 1605, as may be desired) to the scissor jack assembly 1674 to controllably extend or retract the camera 1610 from the camera storage well 1676 by sliding the retraction controller 1670 as shown by arrow 1671. The scissor jack assembly 1674 may include at least two support arms, such as first and second support arms 1675 and 1677, respectively, which may be pivotably coupled to each other at pivot 1679. Further, ends of the support arms 1675, 1677 may be pivotably coupled by pins passing through holes or slots in the distal end portion 1606 and camera base 1678, similar to that described in connection with FIG. 13.

At least one cable 1638 in a channel 1607 (shown in FIG. 18 and being similar to channels 107, 807 described in connection with other embodiments) may couple the end portion controller 1620 to the cylinder 1680 and/or to the scissor jack assembly 1674 such as two cables, one cable to control an instrument or a tool, such as control and/or effectuate movement of the scissor jack assembly 1674 or any other type of assembly and/or surgical tools, and another cable to control and/or effectuate movement of imaging device(s) such as to rotate the cylinder 1680, e.g., to rotate the camera 1610 about a longitudinal axis of the cylinder 1680 and/or extend/retract the camera 1610.

The imaging device(s) at the distal end of the endoscopic microinstrument may include optics, detectors, filters such as the Conjugated Multi-Bandpass Filters (CMBFs) for 3D-visualization, CMOS or CCD detectors and processors to process images detected by the detectors and provide video signals to a display(s) or monitor(s) for 2D and/or 3D display of images captured by the imaging device(s) for viewing by a viewer(s). Imaging devices for capturing 3D images include those having CMBFs such as described in U.S. Patent Application Publication Nos. 2011/0115882 and 2014/0085420 to Shahinian et al., which are incorporated herein by reference in their entirety.

Figure 17:
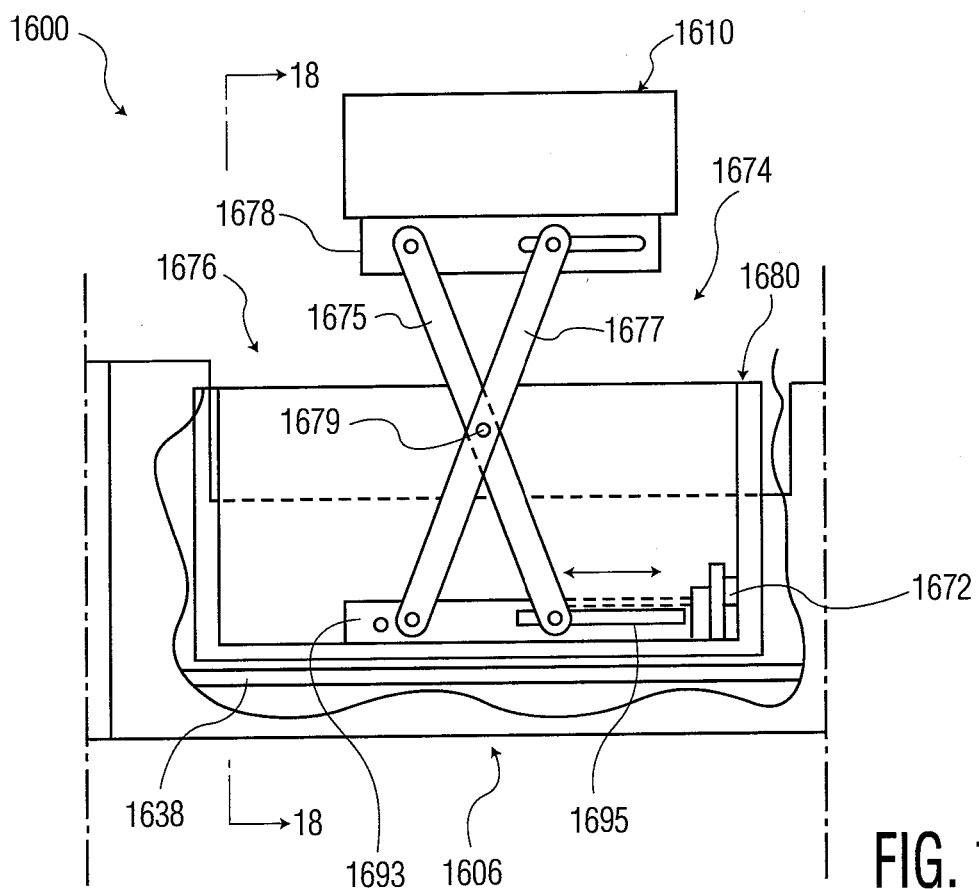
FIG. 17 shows a partially cutaway detailed side view of a portion of an endoscopic microinstrument of FIG. 16 in accordance with embodiments of the present system.

FIG. 17 shows a partially cutaway detailed side view of a portion of an endoscopic microinstrument 1600 of FIG. 16 in accordance with embodiments of the present system. The camera 1610 is shown in the extended position. Further, a biasing member may be provided to extend and/or retract the camera 1610, if desired. Further, a locking mechanism may be provided to lock the camera 1610 in the extended and/or retracted position, if desired. The scissor jack assembly 1674 may include a base portion 1693 which is coupled to the cylinder 1680. The base portion 1693 may include at least one extended opening 1695 or slot to provide for slidable motion of at least one of the first and second support arms 1675 and 1677, respectively, such as the first support arms 1675.

Figure 18:
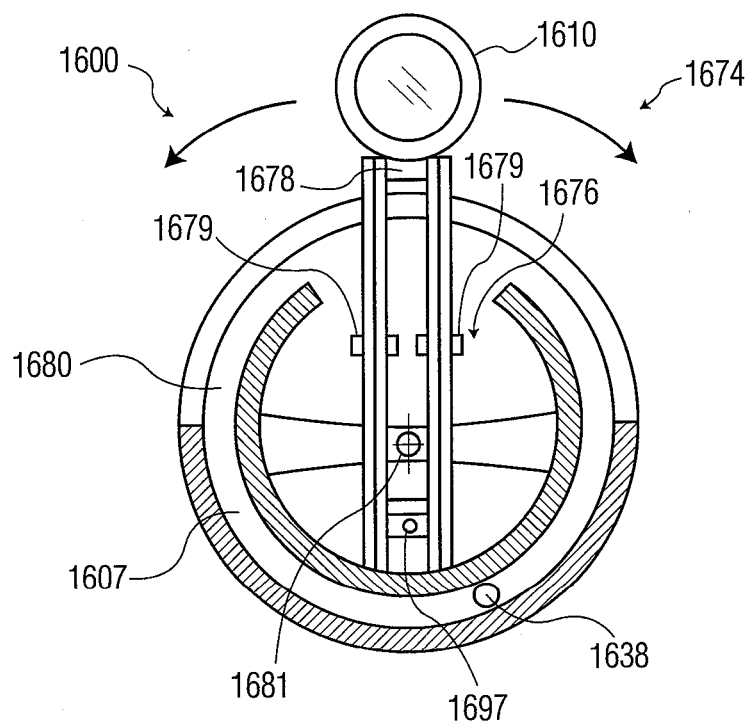
FIG. 18 shows a cross sectional view of a portion of the endoscopic microinstrument taken along lines 18-18 of FIG. 17 in accordance with embodiments of the present system.

FIG. 18 shows a cross sectional view of a portion of the endoscopic microinstrument taken along lines 18-18 of FIG. 17 in accordance with embodiments of the present system. The at least one cable 1638 may be coupled to at least one of the first and second support arms 1675 and 1677, respectively, such as the first support arms 1675 via a coupler 1697. Further, a linkage 1681, similar to the linkage 881 (FIG. 11) may be provided to couple the camera 1610 to the end portion controller 1620. In some embodiments, the first and second support arms may each comprise a single arm formed in an X configuration.

Figure 19:
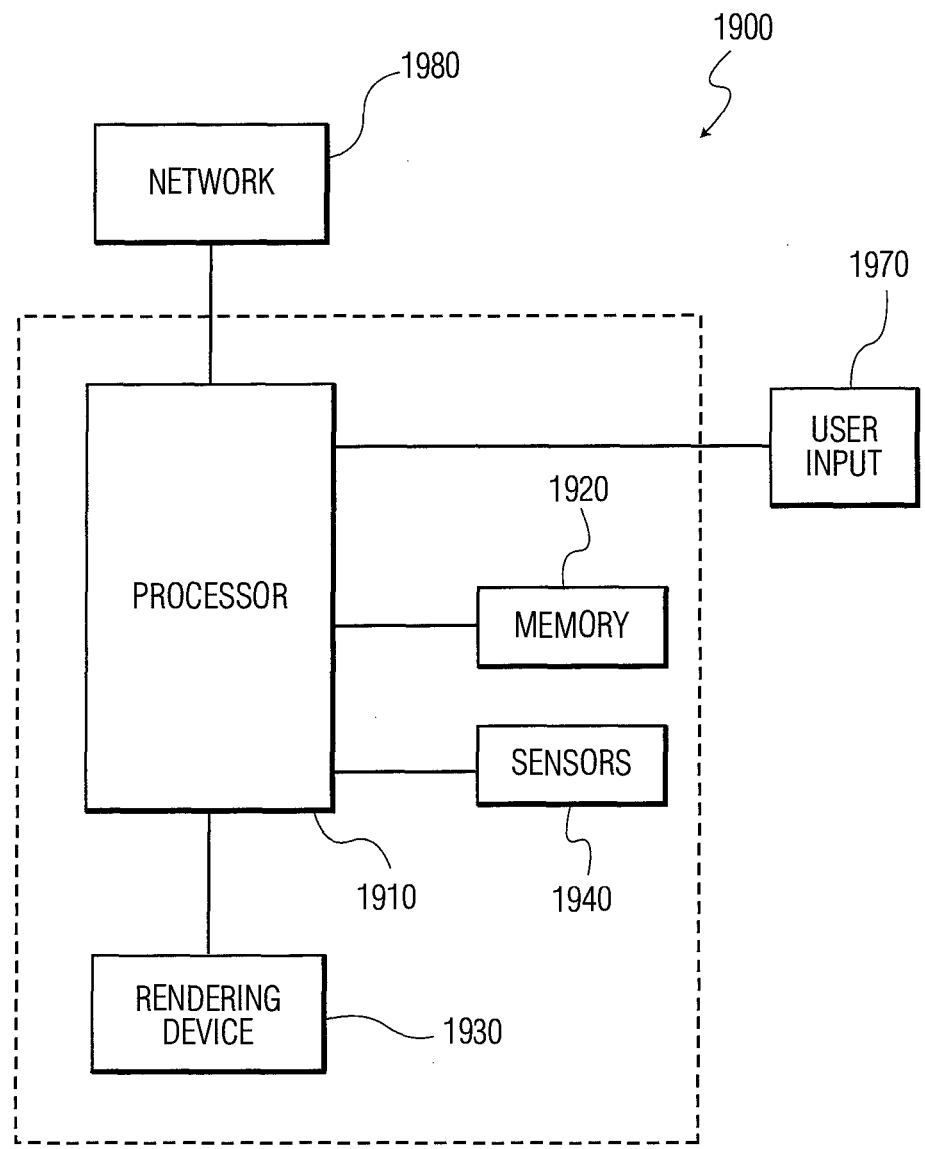
FIG. 19 shows a portion of a system 1900 in accordance with embodiments of the present system.

FIG. 19 shows a portion of a system 1900 in accordance with embodiments of the present system. For example, a portion of the present system may include a processor 1910 (e.g., a controller) operationally coupled to a memory 1920, a rendering device such as a display 1930, sensors 1940, and a user input device 1970. The memory 1920 may be any type of device for storing application data as well as other data related to the described operation. The application data and other data are received by the processor 1910 for configuring (e.g., programming) the processor 1910 to perform operation acts in accordance with the present system. The processor 1910 so configured becomes a special purpose machine particularly suited for performing in accordance with embodiments of the present system.

The user input 1970 may include a keyboard, a mouse, a trackball, or other device, such as a touch-sensitive display, which may be stand alone or be a part of a system, such as part of a personal computer, a personal digital assistant (PDA), a mobile phone (e.g., a smart phone), a monitor, a smart- or dumb-terminal or other device for communicating with the processor 1910 via any operable link. The user input device 1970 may be operable for interacting with the processor 1910 including enabling interaction within a user interface (UI) as described herein. Clearly the processor 1910, the memory 1920, display 1930, and/or user input device 18 70 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a non-transitory computer-readable medium, such as an integrated chip, a peripheral device or memory, such as the memory 1920 or other memory coupled to the processor 1910.

The program and/or program portions contained in the memory 1920 may configure the processor 1910 to implement the methods, operational acts, and functions disclosed herein. The memories may be distributed, for example between the clients and/or servers, or local, and the processor 1910, where additional processors may be provided, may also be distributed or may be singular. The memories may be implemented as electrical, magnetic or optical memory, or any combination of these or other types of storage devices.

Moreover, the term "memory" should be construed broadly enough to encompass any information able to be read from or written to an address in an addressable space accessible by the processor 1910. With this definition, information accessible through a network is still within the memory, for instance, because the processor 1910 may retrieve the information from the network for operation in accordance with the present system.

The processor 1910 is operable for providing control signals and/or performing operations in response to input signals from the user input device 1970 as well as in response to other devices of a network and executing instructions stored in the memory 1920. The processor 1910 may include one or more of a microprocessor, an application-specific or general-use integrated circuit(s), a logic device, etc. Further, the processor 1910 may be a dedicated processor for performing in accordance with the present system or may be a general-purpose processor wherein only one of many functions operates for performing in accordance with the present system. The processor 1910 may operate utilizing a program portion, multiple program segments, or may be a hardware device utilizing a dedicated or multi-purpose integrated circuit. Embodiments of the present system may provide fast imaging methods to acquire images and generate corresponding image information.

In accordance with some embodiments, electronic actuators may be provided to extend, retract, and/or rotate the camera in accordance with inputs from a user interface such as including one or more joysticks which may replace, at least partially, functions of the end portion controller and/or dispense with having the scissor type controls having the handles 112, 116. Thus, a tool joystick may replace the scissor type controls for controlling 3D movement of a distal tool. Such a tool joystick may be in addition to other joysticks for providing 3D movement controls of other devices such as one or more 2D and/or 3D cameras located at the distal end of an any instrument such as an endoscope, near further devices such as tools configured to provide desired functions, such as grippers, cutters, dissector, ultrasonic aspirators, light sources, communication links, coagulators, lasers, imagers including 2D and/or 3D cameras with optics, CMBF's and processors that provide video signals for rendering 2D and/or 3D images, etc. For example, the endoscopic microinstrument system may include a joystick-1 for controlling camera-1, a joystick-2 for controlling camera-2, a joystick-3 for controlling tool-1, a joystick-4 for controlling tool-2, etc.

The further joysticks or controls may provide movement control (e.g., in any desired 3D direction, such as articulation, rotation, translation in any desired 3D direction, such as right, left, front (extension), back (retraction) directions) to move the distal tool independently of the camera control, if desired. For example, additional joysticks and/or user interfaces (e.g., hard or soft), such knobs, buttons, keys, may be provided to activate further devices, such as further tools and cameras, etc. The controllers (e.g., joysticks) and the controlled devices (e.g., tools, cameras) may be operationally coupled and connected to communicate with each other (e.g., via wired or wireless links) such that the controllers and the controlled devices may be reconfigured, e.g., by a processor, under the control of computer instructions stored in a memory or any non-transitory computer readable medium for effectuating 3D movement of the tools and desired operations of the tools, cameras, and/or controller (e.g., joysticks). Accordingly, a versatile endoscopic microinstrument that includes a combination distal tool(s) and distal camera(s) is provided that can 'see' an ROI where a distal tool may be manipulated. Different tools or tools with different functions and/or camera(s) can be independently and/or synchronously controlled via one or more controllers, such as joysticks, knobs, buttons, couplers and the like, which may be a combination of hard and soft buttons on a UI, such as a displayed UI displayed on a touch sensitive screen, for example.

Further, having a camera(s) at the distal end of the endoscopic microinstrument near the tool(s) (instead of having the camera at the proximal end) allows for camera movement that tracks movement of the tool and thus have the camera 'see' what the tool is looking at, including providing a rear view, such as when the tool is also rotated to point to the rear which maybe pointing 180° or directly backwards relative a front direction and/or any angle relative the front view between 0 and 160°, between 0 and 140° and/or between 0 and 120°, for example. In addition to such synchronous movements between the camera and tool, the camera or a further camera may be decoupled for independent control to move independently of the tool movement and point to a desired direction different from a direction the tool is pointing to. A decoupled camera-tool combination maybe re-coupled or re-syncronize, such as in response to a synchronization (sync) signal from a controller or processor to re-syncronize the camera and tool together, again, where the camera follows the tool or moves together with the tool and/or the distal tip of the endoscopic microinstrument including the tool, for example.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. An endoscopic microinstrument, comprising:
a substantially rigid body having first and second ends, a channel between the first and second ends;
a substantially rigid end portion movably coupled to the body and having first and second ends;
a tool located at the first end of the substantially rigid end portion and comprising first and second anvils;
first and second handles coupled to the body, at least one of the handles further coupled to the tool and configured to control actuation of at least one of the first and second anvils;
a camera coupled to, and situated to a side of, the substantially rigid end portion, the camera configured to obtain images of a region-of-interest; and
an end portion controller coupled to the body and configured to rotate the substantially rigid end portion relative to the substantially rigid body to angulate and/or rotate the tool and the camera together or separately so that a line of sight of the camera is along a tool axis passing through the tool,
wherein the end portion controller is further configured to rotate the camera relative to the substantially rigid end portion.

2. The endoscopic microinstrument of claim 1, further comprising a flexible portion which couples the substantially rigid end portion to the substantially rigid body and is situated between the substantially rigid body and the substantially rigid end portion.

3. The endoscopic microinstrument of claim 1, wherein the camera is a wireless-type camera and is situated outside of an exterior periphery of the substantially rigid end portion.

4. The endoscopic microinstrument of claim 1, wherein a longitudinal axis of a lens of the camera is parallel to and offset from a longitudinal axis of the substantially rigid end portion.

5. The endoscopic microinstrument of claim 1, wherein the tool comprises at least one of a surgical gripper, a cutter, a coagulator, a dissector, a laser, laparoscope, and an ultrasonic tool including for ablation, pulverization, aspiration or otherwise.

6. An endoscopic microinstrument, comprising:
a substantially rigid body having first and second ends, a channel between the first and second ends;
a substantially rigid end portion movably coupled to the body and having first and second ends;
a tool located at the first end of the substantially rigid end portion and comprising first and second anvils;
first and second handles coupled to the body, at least one of the handles further coupled to the tool and configured to control actuation of at least one of the first and second anvils;
a camera coupled to, and situated to a side of, the substantially rigid end portion, the camera configured to obtain images of a region-of-interest; and
an end portion controller coupled to the body and configured to rotate the substantially rigid end portion relative to the substantially rigid body to angulate and/or rotate the tool and the camera together or separately so that a line of sight of the camera is along a tool axis passing through the tool,
wherein the camera further comprises a rotational mount to rotate the camera or the substantially rigid end portion about a longitudinal axis of the substantially rigid end portion independent of rotation of the tool.

7. An endoscopic microinstrument, comprising:
a body having a channel;
an end portion at a distal end of the endoscopic microinstrument, the end portion having a first end for being movably coupled to the body;
a tool located at a second end of end portion distal from the first end of the end portion for being located at the distal end for manipulating a region-of-interest;
a camera coupled to, and situated to a side of, the end portion, the camera being configured to obtain images of the region-of-interest; and
an end portion controller located at a proximate end of the endoscopic microinstrument, opposite the distal end, the end portion controller being coupled to the body and configured to rotate the end portion relative to the body to angulate and/or rotate the tool and the camera together or separately,
wherein the camera is extendable and retractable from a storage well of the end portion under control of one of the end portion controller and a further controller.

8. The endoscopic microinstrument of claim 7, further comprising a flexible portion which couples the end portion to the body and is situated between the body and the end portion.

9. The endoscopic microinstrument of claim 7, wherein the end portion controller includes at least one of:
a tool controller configured to control at least one of a function and a movement of the tool;
a camera controller configured to control at least one of a function and a movement of the camera; and
an end portion controller configured to control a movement of the end portion;
portion.

10. The endoscopic microinstrument of claim 7, wherein a longitudinal axis of a lens of the camera is parallel to and offset from a longitudinal axis of the substantially rigid end portion.

11. An endoscopic microinstrument, comprising:
a body having a channel;
an end portion at a distal end of the endoscopic microinstrument, the end portion having a first end for being movably coupled to the body;

a tool located at a second end of end portion distal from the first end of the end portion for being located at the distal end for manipulating a region-of-interest;

a camera coupled to, and situated to a side of, the end portion, the camera being configured to obtain images of the region-of-interest; and an end portion controller located at a proximate end of the endoscopic microinstrument, opposite the distal end, the end portion controller being coupled to the body and configured to rotate the end portion relative to the body to angulate and/or rotate the tool and the camera together or separately, wherein the end portion controller is further configured to rotate the camera relative to the end portion.

12. An endoscopic microinstrument, comprising:

a body having a channel;

an end portion at a distal end of the endoscopic microinstrument, the end portion having a first end for being movably coupled to the body;

a tool located at a second end of end portion distal from the first end of the end portion for being located at the distal end for manipulating a region-of-interest;

a camera coupled to, and situated to a side of, the end portion, the camera being configured to obtain images of the region-of-interest; and an end portion controller located at a proximate end of the endoscopic microinstrument, opposite the distal end, the end portion controller being coupled to the body and configured to rotate the end portion relative to the body to angulate and/or rotate the tool and the camera together or separatelywherein the camera further comprises a rotational mount to rotate the camera or the end portion about a longitudinal axis of the end portion independent of rotation of the tool.

13. An endoscopic microinstrument, comprising:

a body having a channel;

an end portion at a distal end of the endoscopic microinstrument, the end portion having a first end for being movably coupled to the body;

a tool located at a second end of end portion distal from the first end of the end portion for being located at the distal end for manipulating a region-of-interest;

a camera coupled to the end portion, the camera being configured to obtain images of the region-of-interest; and a plurality of controllers located at a proximate end of the endoscopic microinstrument, opposite the distal end, and being configured to control at least one of a function and a movement of at least one of the tool and the camera for synchronous movement together or independent movement, wherein the camera is extendable and retractable from a storage well of the end portion under control of one of the plurality of controllers.

14. The endoscopic microinstrument of claim 13, wherein the plurality of controllers includes:

a tool controller configured to control at least one of a function and a movement of the tool;

a first camera controller configured to control at least one of a function and a movement of the camera;

a second camera controller configured to control extension and retraction of the camera from the storage well; and an end portion controller configured to control a movement of the end portion.

15. The endoscopic microinstrument of claim 13, wherein the camera is a wireless-type camera and is situated outside of an exterior periphery of the end portion for capturing and providing one of 2-dimensional (2D) and 3-dimensional (3D) images of the region-of-interest.

16. An endoscopic microinstrument, comprising:

a body having a channel;

an end portion at a distal end of the endoscopic microinstrument, the end portion having a first end for being movably coupled to the body;

a tool located at a second end of end portion distal from the first end of the end portion for being located at the distal end for manipulating a region-of-interest;

a camera coupled to the end portion, the camera being configured to obtain images of the region-of-interest; and a plurality of controllers located at a proximate end of the endoscopic microinstrument, opposite the distal end, and being configured to control at least one of a function and a movement of at least one of the tool and the camera for synchronous movement together or independent movement wherein the camera further comprises a rotational mount to rotate the camera or the end portion about a longitudinal axis of the end portion independent of rotation of the tool.

* * * * *